United States Patent
Lee et al.

(10) Patent No.: US 11,213,693 B2
(45) Date of Patent: Jan. 4, 2022

(54) LIGHT SOURCE FOR EYE THERAPY AND LIGHT EMITTING DEVICE HAVING THE SAME

(71) Applicant: Seoul Viosys Co., Ltd., Ansan-si (KR)

(72) Inventors: A Young Lee, Ansan-si (KR); Yeong Min Yoon, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 84 days.

(21) Appl. No.: 16/394,850

(22) Filed: Apr. 25, 2019

(65) Prior Publication Data

US 2019/0329064 A1    Oct. 31, 2019

Related U.S. Application Data

(60) Provisional application No. 62/663,983, filed on Apr. 27, 2018.

(51) Int. Cl.
*A61N 5/06* (2006.01)

(52) U.S. Cl.
CPC .... *A61N 5/0613* (2013.01); *A61N 2005/0648* (2013.01); *A61N 2005/0651* (2013.01); *A61N 2005/0663* (2013.01)

(58) Field of Classification Search
CPC .......... A61N 5/0613; A61N 2005/0648; A61N 2005/0651; A61N 2005/0663
See application file for complete search history.

(56) References Cited

U.S. PATENT DOCUMENTS

| | | | | |
|---|---|---|---|---|
| 2011/0285295 | A1* | 11/2011 | Son | H05B 45/24 315/152 |
| 2013/0238060 | A1* | 9/2013 | Nevins | A61N 5/0613 607/90 |
| 2017/0361124 | A1* | 12/2017 | Parker | A61N 5/0613 |
| 2018/0139817 | A1* | 5/2018 | Yamakawa | H01L 33/56 |
| 2018/0351050 | A1* | 12/2018 | Yamakawa | A61N 5/06 |

FOREIGN PATENT DOCUMENTS

| | | | | |
|---|---|---|---|---|
| JP | WO 2016/208683 A1 * | 12/2016 | | H01L 33/00 |
| JP | 6175210 | 8/2017 | | |
| JP | WO 2017/135255 A1 * | 8/2017 | | A61F 9/00 |

OTHER PUBLICATIONS

Pei-Chang Wu et al., "Outdoor Activity during Class Recess Reduces Myopia Onset and Progression in School Children," American Academy of Ophthalmology 2013; pp. 1080-1085.

Dongmei Cui et al., "Effect of Day Length on Eye Growth, Myopia Progression, and Change of Corneal Power in Myopic Children," American Academy of Ophthalmology 2013; pp. 1074-1079.

(Continued)

*Primary Examiner* — Nathan J Jenness

(74) *Attorney, Agent, or Firm* — H.C. Park & Associates, PLC

(57) ABSTRACT

A light source for eye therapy configured to emit light having a wavelength range from about 380 nm to about 780 nm, and has a spectrum area that overlaps at least about 55% of an area of a normalized solar spectrum, in which a peak wavelength of light has a deviation equal to or less than about 0.14 from the normalized solar spectrum in a wavelength range from about 380 nm to about 490 nm.

19 Claims, 15 Drawing Sheets

(56) References Cited

OTHER PUBLICATIONS

Justin C. Sherwin et al., "The Association between Time Spent Outdoors and Myopia in Children and Adolescents—A Systematic Review and Meta-analysis," American Academy of Ophthalmology 2012; pp. 119: 2141-2151.

Mingguang He et al., "Effect of Time Spent Outdoors at School on the Development of Myopia Among Children in China—A Randomized Clinical Trial," Jama.com 2015, vol. 314, No. 11; pp. 1142-1148.

Dongmei Cui et al., "Outdoor Recess Time Can Reduce the Risk of Nearsightednss in Children," American Academy of Ophthalmology, 2013, pp. 1-3.

Chinese Office Action dated Nov. 2021, for Chinese Patent Application No. 201980003007.X. (with Concise English Explanation).

\* cited by examiner

LIGHT SOURCE FOR EYE THERAPY AND LIGHT EMITTING DEVICE HAVING THE SAME

CROSS-REFERENCE TO RELATED APPLICATION

This application claims the benefit of U.S. Provisional Application No. 62/663,983, filed on Apr. 27, 2018, which is hereby incorporated by reference for all purposes as if fully set forth herein.

BACKGROUND

Field

Exemplary embodiments of the invention relate generally to a light source for eye therapy and, more specifically, to a light source for eye therapy and a light emitting device having the same.

Discussion of the Background

Today's people tend to not only overstrain their eyes from using computers or watching TVs, but also have a life pattern that involves in much indoor activities rather than outdoor works. As such, people don't get enough sunlight due to their lifestyles, and lack of adequate sunlight may cause problems, such as short sightedness.

The above information disclosed in this Background section is only for understanding of the background of the inventive concepts, and, therefore, it may contain information that does not constitute prior art.

SUMMARY

Exemplary embodiments of the invention provide a light source having a spectrum close to sunlight and a light emitting device having the light source.

Additional features of the inventive concepts will be set forth in the description which follows, and in part will be apparent from the description, or may be learned by practice of the inventive concepts A light source for eye therapy according to an exemplary embodiment is configured to emit light having a wavelength range from about 380 nm to about 780 nm, and has a spectrum area that overlaps at least about 55% of an area of a normalized solar spectrum, in which a peak wavelength of light has a deviation equal to or less than about 0.14 from the normalized solar spectrum in a wavelength range from about 460 nm to about 490 nm.

A valley wavelength of light may have a deviation equal to or less than about 0.15 from the normalized solar spectrum in the wavelength range from about 380 nm to about 490 nm.

A color temperature of light may be in a range of about 2600K to about 7000K.

The spectrum area of light may overlap at least about 55% of the area of the normalized solar spectrum when the color temperature of light is in a range of about 2600K to about 3700K.

A peak wavelength of light may have a deviation equal to or less than about 0.10 from the normalized solar spectrum.

The spectrum area of light may overlap at least about 70% of the area of the normalized solar spectrum when the color temperature of light is in a range from about 3700K to about 4700K.

A peak wavelength of light may have a deviation equal to or less than about 0.13 from the normalized solar spectrum.

The spectrum area of light may overlap at least about 75% of the area of the normalized solar spectrum when the color temperature of light is in a range from about 4700K to about 7000K.

A peak wavelength of light may have a deviation equal to or less than about 0.14 from the normalized solar spectrum.

A light source for eye therapy according to another exemplary embodiment is configured to emit light having a color temperature in a range of about 2600K to about 7000K, in which a spectrum area of light overlaps at least about 55% of an area of a normalized solar spectrum.

A peak wavelength of light may have a deviation equal to or less than about 0.14 from the normalized solar spectrum.

The normalized solar spectrum may be represented by $$E(\lambda, T) = \frac{2hc^2}{\lambda^5} \cdot \frac{1}{e^{hc/\lambda kT} - 1}$$

where $\lambda$, h, c, T, and k denote a wavelength (um), Planck's constant, a speed of light, an absolute temperature, and Boltzmann's constant, respectively.

The light source may be used for treating myopia.

The light source may be used for reducing eye stress.

A light emitting device for eye therapy may include the light source according to an exemplary embodiments and a control unit for controlling the light source.

The light emitting device may further include a mounting member connected to the light source to be mounted on a user's head.

The light emitting device may further include a supporting member for supporting the light source to be provided as a table lamp.

A light emitting diode for eye therapy according to yet another exemplary embodiment includes a first light source configured to emit light having a first wavelength range from about 380 nm to about 780 nm, wherein a spectrum area of light overlaps at least about 55% of an area of a normalized solar spectrum in a color temperature from about 2600K to about 7000K, a second light source configured to emit light having a second wavelength range different from the first wavelength range, a location information receiving unit configured to detect a location of the light emitting diode, and a control unit configured to adjust the amount of light emitted from the first and second light sources in response to information obtained from the location information receiving unit.

The light emitting diode may further include a third light source configured to emit light in an infrared wavelength range, in which the location information receiving unit comprises a global positioning system, and the second wavelength range is different from the infrared wavelength range.

A peak wavelength of light emitted from the first light source may have a deviation equal to or less than about 0.14 from the normalized solar spectrum in a wavelength range from about 380 nm to about 490 nm, and a valley wavelength of light emitted from the first light source may have a deviation equal to or less than about 0.15 from the normalized solar spectrum in the wavelength range from about 450 nm to about 530 nm.

It is to be understood that both the foregoing general description and the following detailed description are exemplary and explanatory and are intended to provide further explanation of the invention as claimed

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
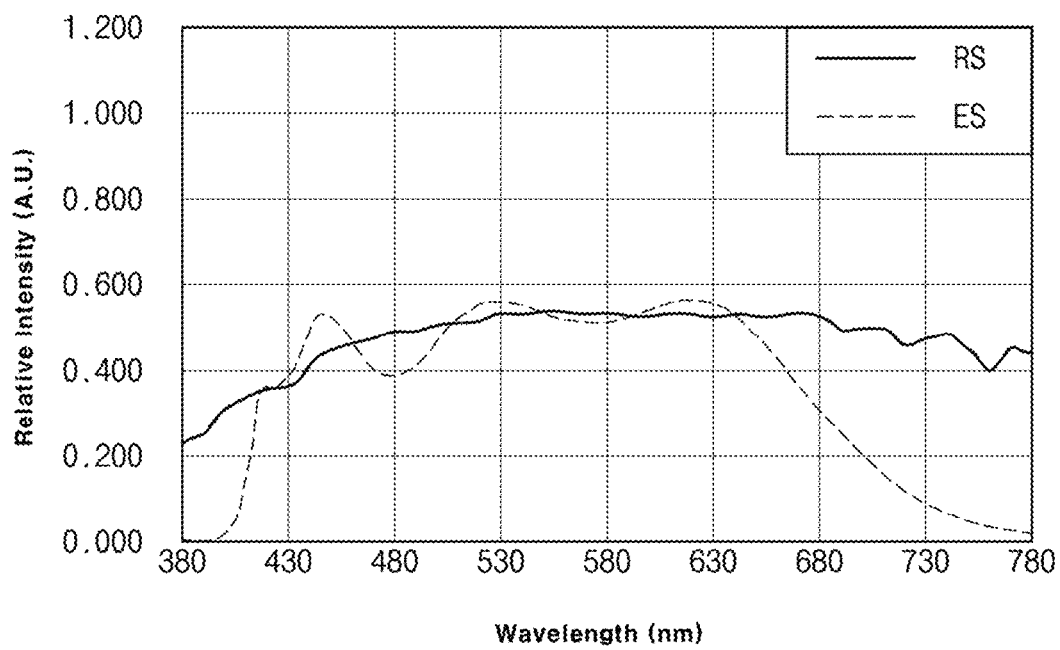
FIG. 1 is a graph showing a spectrum of a light source according to an exemplary embodiment and a solar spectrum.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein Exemplary embodiments relate to a light source for eye therapy, which may emit light similar to sunlight. In some exemplary embodiments, the light source may emit light having a spectrum very similar to that of the sunlight and be used to treat or prevent diseases, such as myopia in a human eye, and to alleviate eye stress by applying the light to the human eye.

Hereinafter, exemplary embodiments of the present disclosure will be explained in detail with reference to the accompanying drawings.

FIG. 1 is a graph showing a spectrum of a light source according to an exemplary embodiment and a solar spectrum. In FIG. 1, an x-axis represents a wavelength (nm), a y-axis represents a relative intensity, a spectrum indicated by "RS" represents a solar spectrum, and a spectrum indicated by "ES" represents a spectrum of light emitted from the light source according to an exemplary embodiment. The solar spectrum may correspond to a color temperature of about 5000K.

Referring to FIG. 1, the light source according to an exemplary embodiment has a spectrum similar to the sunlight. However, light emitted from the light source according to the exemplary embodiment may be different from the sunlight, in that the light source emits light having a wavelength range that at least corresponds to a portion of a visible light, which excludes most of an ultraviolet wavelength range that may be harmful when applied to the human eye. The light source according to an exemplary embodiment may emit light having a wavelength range from about 380 nm to about 780 nm, which may substantially correspond to an entire wavelength range of visible light.

The light source according to an exemplary embodiment may emit light corresponding to a portion of the wavelength range of the visible light, instead of the entire wavelength of the visible light, for example, light having a wavelength range from about 400 nm to about 630 nm.

As used herein, the term "similar to the sunlight" refers that an overlapping area between a spectrum of a light source and the solar spectrum is equal to or greater than a predetermined value, and a deviation of the peak from the solar spectrum (e.g., a degree of the deviation with respect to a peak wavelength of the solar spectrum) is equal to or less than a predetermined value, when compared with a conventional art with respect to a normalized solar spectrum. For example, the light source according to an exemplary embodiment may emit light having a spectrum area equal to or greater than about 55% of an area of the normalized solar spectrum, and the peak wavelength of light may have the deviation equal to or less than about 0.14 from the normalized solar spectrum.

The normalized solar spectrum may be represented by the following Equation 1.

$$E(\lambda, T) = \frac{2hc^2}{\lambda^5} \cdot \frac{1}{e^{hc/\lambda kT} - 1} \quad \text{[Equation 1]}$$

λ: wavelength (um)
h: Planck's constant
c: speed of light
T: absolute temperature
k: Boltzmann's constant In addition, the sunlight may have various color temperatures depending on the time of the day, and the light source according to an exemplary embodiment may emit light having a spectrum similar to the sunlight having different color temperatures.

For example, the light source according to an exemplary embodiment may emit a warm white light having the color temperature of about 2600K to about 3700K, which is similar to the sunlight in the evening. In addition, the light source according an exemplary embodiment may emit a natural white light having the color temperature of about 3700K to about 4700K, which is similar to the sunlight in the morning. As another example, the light source according an exemplary embodiment may emit a cool white light having the color temperature of about 4700K to about 7000K, which is similar to the sunlight at noon.

FIGS. 2A to 2E are graphs showing the spectrum of the light source as a function of the color temperature according to an exemplary embodiment. Hereinafter, in the spectrum of light, the x-axis represents the wavelength (nm), the y-axis represents the relative intensity, the spectrum indicated by "RS" represents the solar spectrum, and the spectrum indicated by "ES" represents the spectrum of light emitted from the light source according to an exemplary embodiment.

Figure 2A:
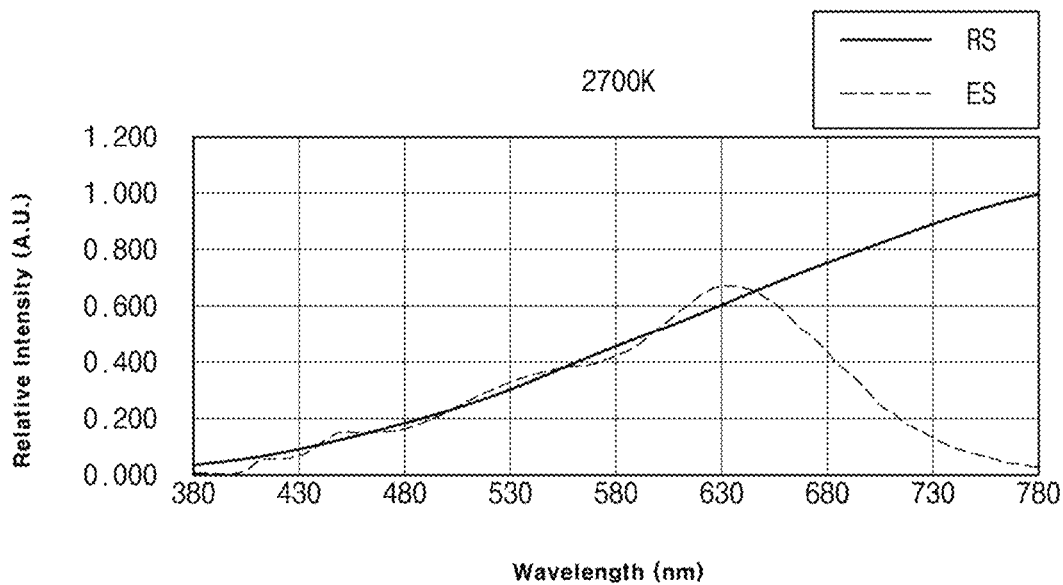
FIGS. 2A, 2B, 2C, 2D, and 2E are graphs showing a spectrum of a light source as a function of a color temperature according to an exemplary embodiment.

Referring to FIG. 2A, when the color temperature is about 2700K, light emitted from the light source according to an exemplary embodiment has the spectrum similar to the sunlight in the wavelength range from about 380 nm to about 780 nm, which corresponds to a visible light range, and particularly has the spectrum substantially similar to the sunlight in the wavelength range from about 380 nm to about 650 nm.

When the color temperature is in a range from about 2600K to about 2800K, e.g., about 2700K, light emitted from the light source according to an exemplary embodiment may have the spectrum area equal to or greater than about 55%, e.g., about 59%, of the normalized solar spectrum, and light may have the peak deviation equal to or less than about 0.10, e.g., about 0.07, with respect to the area of the normalized solar spectrum.

As used herein, a peak deviation is a value indicating how far the value of the highest peak in a predetermined area of the spectrum of the light source deviates from that in the corresponding solar spectrum. The method of obtaining the peak deviation will be described later in more detail with reference to FIG. 3.

Figure 2B:
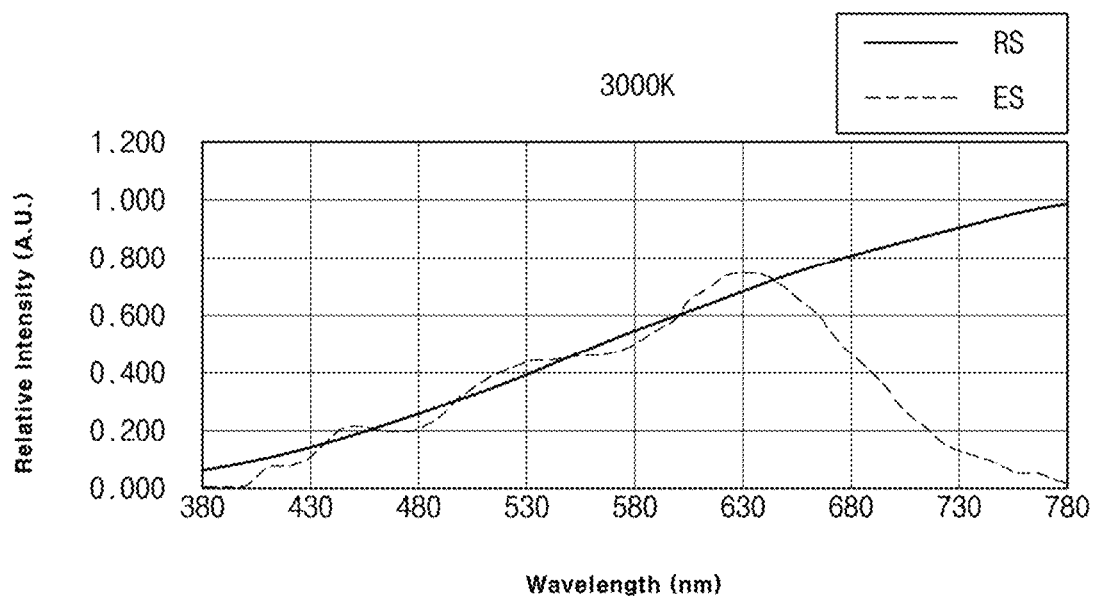

Referring to FIG. 2B, when the color temperature is about 3000K, light emitted from the light source according to an exemplary embodiment has the spectrum similar to the sunlight in the wavelength range from about 380 nm to about 780 nm, which corresponds to the visible light range, and particularly has the spectrum substantially similar to the sunlight in the wavelength range from about 380 nm to about 640 nm.

When the color temperature is in a range from about 2800K to about 3700K, e.g., about 3000K, light emitted from the light source according to an exemplary embodiment may have the spectrum area equal to or greater than about 55%, e.g., about 62%, of the normalized solar spectrum, and light may have the peak deviation equal to or less than about 0.10, e.g., about 0.07, with respect to the area of the normalized solar spectrum.

Figure 2C:
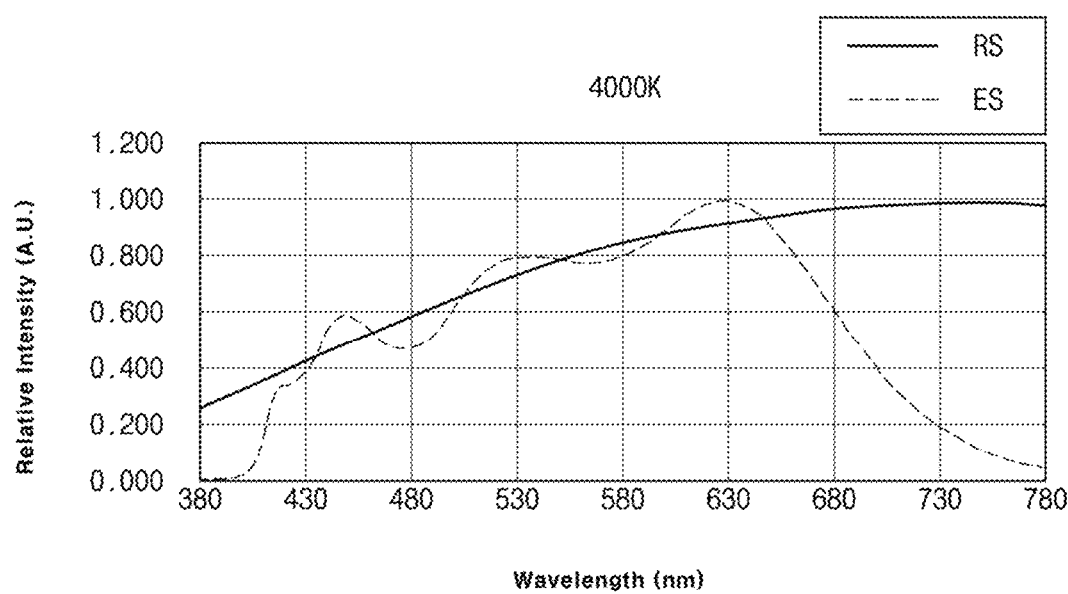

Referring to FIG. 2C, when the color temperature is about 4000K, light emitted from the light source according to an exemplary embodiment has the spectrum similar to the sunlight in the wavelength range from about 380 nm to about 780 nm, which corresponds to the visible light range, and particularly has the spectrum substantially similar to the sunlight in the wavelength range from about 400 nm to about 650 nm.

When the color temperature is in a range from about 3700K to about 4700K, e.g., about 4000K, light emitted from the light source according to an exemplary embodiment may have the spectrum area equal to or greater than about 65%, e.g., about 70%, of the normalized solar spectrum, and light may have the peak deviation equal to or less than about 0.13, e.g., about 0.11, with respect to the area of the normalized solar spectrum.

Figure 2D:
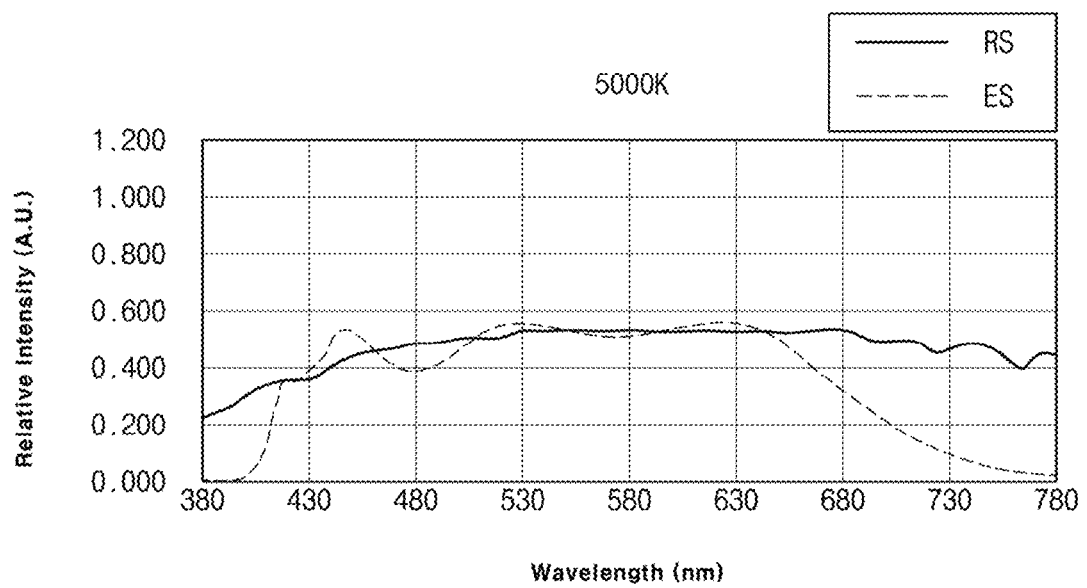

Referring to FIG. 2D, when the color temperature is about 5000K, light emitted from the light source according to an exemplary embodiment has the spectrum similar to the sunlight in the wavelength range from about 380 nm to about 780 nm, which corresponds to the visible light range, and particularly has the spectrum substantially similar to the sunlight in the wavelength range from about 400 nm to about 640 nm.

When the color temperature is in a range from about 4700K to about 5800K, e.g., about 5000K, light emitted from the light source according to an exemplary embodiment may have the spectrum area equal to or greater than about 70%, e.g., about 75%, of the normalized solar spectrum, and light may have the peak deviation equal to or less than about 0.13, e.g., about 0.10, with respect to the area of the normalized solar spectrum.

Figure 2E:
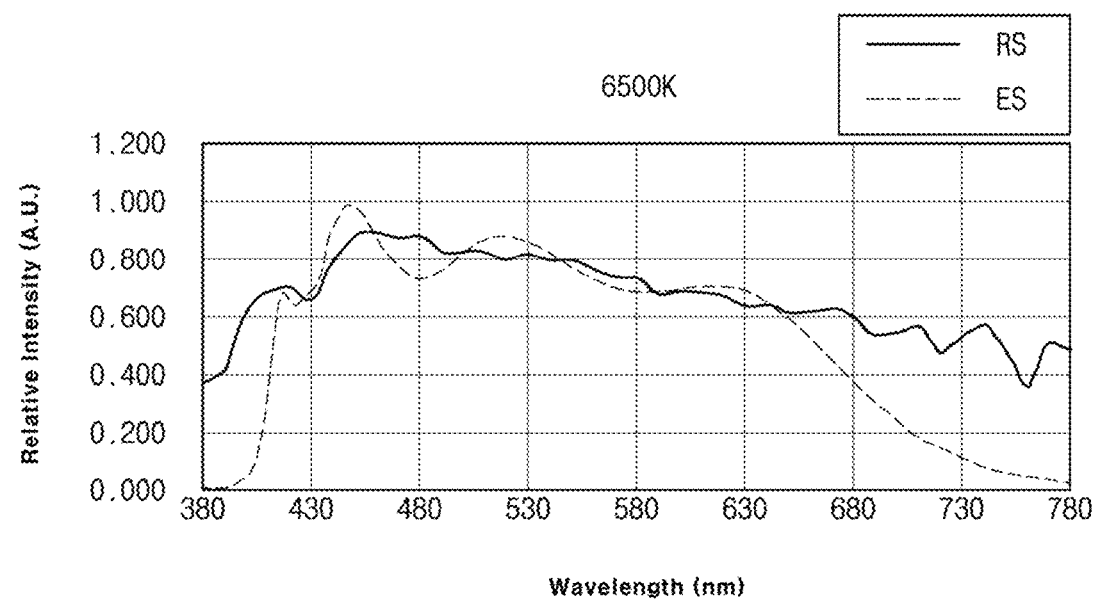

Referring to FIG. 2E, when the color temperature is about 6500K, light emitted from the light source according to an exemplary embodiment has the spectrum similar to the sunlight in the wavelength range from about 380 nm to about 780 nm, which corresponds to the visible light range, and particularly has the spectrum substantially similar to the sunlight in the wavelength range from about 400 nm to about 650 nm.

When the color temperature is in a range from about 5800K to about 7000K, e.g., about 6500K, light emitted from the light source according to an exemplary embodiment may have the spectrum area equal to or greater than about 76%, e.g., about 79%, of the normalized solar spectrum, and light may have the peak deviation equal to or less than about 0.16, e.g., about 0.14, with respect to the area of the normalized solar spectrum.

When considering the spectrum as a whole, when light emitted from the light source has the warm white color temperature of about 2600K to about 3700K, the light may have the spectrum area equal to or greater than about 55% of the normalized solar spectrum, and may have the peak deviation equal to or less than about 0.10 with respect to the area of the normalized solar spectrum.

When light emitted from the light source has the natural white color temperature of about 3700K to about 4700K, the light may have the spectrum area equal to or greater than about 70% of the normalized solar spectrum, and may have the peak deviation equal to or less than about 0.13 with respect to the area of the normalized solar spectrum.

When light emitted from the light source has the cool white color temperature of about 4700K to about 7000K, the light may have the spectrum area equal to or greater than about 75% of the normalized solar spectrum, and may have the deviation equal to or less than about 0.16 with respect to the area of the normalized solar spectrum.

According to the exemplary embodiments, the light source shows a spectrum similar to a solar light, especially at a blue wavelength. A convention light source may generally show a spectrum different from sunlight in the blue wavelength range, particularly, a high peak and a low valley, which deviate much from the sunlight. However, since light emitted from the light source according to the exemplary embodiments shows the spectrum substantially similar to that of the sunlight in the blue wavelength range, almost no peak or valley may appear, or may not stand out even though a peak or valley appears.

Table 1 shows a peak deviation and a valley deviation of the spectrum of the light source according to an exemplary embodiment with respect to the solar spectrum in the wavelength range from about 380 nm to about 490 nm.

TABLE 1

| Color temperature | Peak deviation | Valley deviation |
|---|---|---|
| 2700 K | 0.02 | 0.02 |
| 3000 K | 0.03 | 0.06 |
| 4000 K | 0.11 | 0.12 |
| 5000 K | 0.10 | 0.10 |
| 6500 K | 0.14 | 0.15 |

The peak deviation of the spectrum of the light source according to an exemplary embodiment with respect to the solar spectrum is a value indicating how far the value of the highest peak in a predetermined area of the spectrum of the light source deviates from that of the corresponding solar spectrum. The valley deviation of the spectrum of the light source according to an exemplary embodiment with respect to the solar spectrum is a value indicating how far the value of the lowest valley in the predetermined area of the light source deviates that of the corresponding solar spectrum.

Figure 3:
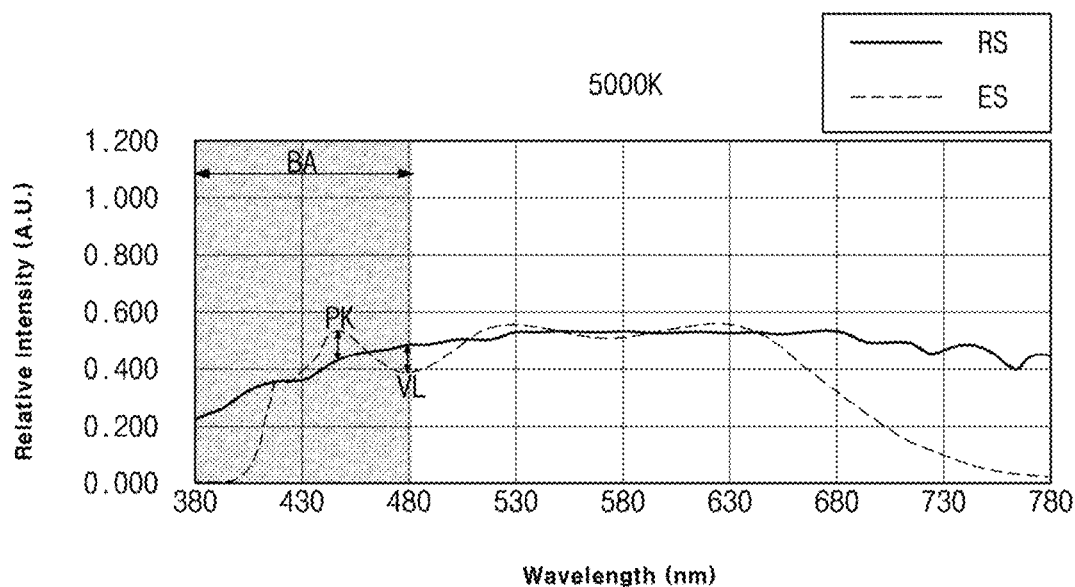
FIG. 3 is a reference diagram illustrating a method of measuring a deviation between a peak and a valley of a spectrum of a light source according to an exemplary embodiment.

The peak deviation and the valley deviation of the light source may be obtained by a method described with reference to FIG. 3 according to an exemplary embodiment. Referring to FIG. 3, an area where the peak and valley deviations are to be checked is indicated by "BA". FIG. 3 exemplarily shows the manner of obtaining the peak and valley deviations in the blue wavelength range. The peak deviation of the spectrum of the light source according to an exemplary embodiment corresponds to a value "PK" obtained by subtracting a value of the solar spectrum from a value of the spectrum of the highest peak in the blue wavelength range. The valley deviation of the spectrum of the light source according to an exemplary embodiment corresponds to a value "VL" obtained by subtracting a value of the spectrum of the lowest valley from the value of the solar spectrum in the wavelength showing the lowest valley of the blue wavelength range.

Referring back to FIGS. 2A to 2E and Table 1, the light source for the therapy according to an exemplary embodiment may emit light having a wavelength range from about 380 nm to about 780 nm, with a spectrum area equal to or greater than about 55% of the area of the normalized solar spectrum, and the peak and valley of the spectrum has a deviation value within a predetermined range in the wavelength range from about 380 nm to about 490 nm. For example, in the wavelength range from about 380 nm to about 490 nm, the peak wavelength of light has the deviation equal to or less than about 0.14 from the normalized solar spectrum, and the valley wavelength has the deviation equal to or less than about 0.15 from the normalized solar spectrum. The deviations may have different values depending on the color temperature. According to FIGS. 2A to 2E, the valley wavelength of the light has the deviation equal to or less than about 0.15 in the wavelength range from about 460 nm to about 490 nm.

Referring to FIG. 2A and Table 1, when the color temperature is in the range from about 2500K to about 2800K, e.g., about 2700K, the peak wavelength of light in the spectrum according to an exemplary embodiment may have the deviation of about 0.02 from the normalized solar spectrum, and the valley wavelength of light may have the deviation of about 0.02 from the normalized solar spectrum.

Referring to FIG. 2B and Table 1, when the color temperature is in the range from about 2800K to about 3500K, e.g., about 3000K, the peak wavelength of light in the spectrum according to an exemplary embodiment may have the deviation of about 0.03 from the normalized solar spectrum, and the valley wavelength of light may have the deviation of about 0.06 from the normalized solar spectrum.

Referring to FIG. 2C and Table 1, when the color temperature is in the range from about 3500K to about 4500K, e.g., about 4000K, the peak wavelength of light in the spectrum according to an exemplary embodiment may have the deviation of about 0.11 from the normalized solar spectrum, and the valley wavelength of light may have the deviation of about 0.12 from the normalized solar spectrum.

Referring to FIG. 2D and Table 1, when the color temperature is in the range from about 4500K to about 5800K, e.g., about 5000K, the peak wavelength of light in the spectrum according to an exemplary embodiment may have the deviation of about 0.10 from the normalized solar spectrum, and the valley wavelength of the light may have the deviation of about 0.10 from the normalized solar spectrum.

Referring to FIG. 2E and Table 1, when the color temperature is in the range from about 5800K to about 7000K, e.g., about 6500K, the peak wavelength of light in the spectrum according to an exemplary embodiment may have the deviation of about 0.14 from the normalized solar spectrum, and the valley wavelength of light may have the deviation of about 0.15 from the normalized solar spectrum.

As described above, the light source according to an exemplary embodiment may emit light having the deviation equal to or less than about 0.15 in the peak and valley wavelengths even when the deviation varies depending on the color temperature. Accordingly, light emitted from the light source according to an exemplary embodiment has the form very similar to the solar spectrum. In particular, in the relatively low color temperature of about 2500K to about 3500K, both of the peak and valley wavelengths have the deviation equal to or less than about 0.10 from the solar spectrum. As a conventional light source has a peak deviation exceeding about 1.0 and a valley deviation exceeding about 0.50, light emitted from the light source according to an exemplary embodiment has the spectrum substantially similar to the sunlight. The spectrum and the peak and valley deviations of the conventional light source may be verified in the experimental example described later.

The light source according to an exemplary embodiment provides a user with light that is similar to the sunlight, except for the wavelength range that is harmful to a human body, for example, ultraviolet light of certain range. As such, the light source may produce substantially the same therapeutic effect as the sunlight without a harmful effect, which will be described in more detail below.

When the sunlight is applied to the human eye, a variety of therapeutic effects may take place. For example, frequent exposure to the sunlight may reduce a prevalence of myopia. Lack of adequate sunlight exposure due to not enough outdoor activity time or the like, a possibility of developing myopia may be increased since the eye may become elliptical while growing long. According to a study by the research team of Zhongshan University in China, the myopia progressed in about 40% of 6-year-old children who did not do any outdoor activities, but the myopia progressed only in about 30% of 6-year-old children who spent about 40 minutes of outdoor activities every day. As the time for outdoor activity increases, the prevalence of myopia may be lowered. In addition, according to a study by the research team of Cambridge University in England, when the hours of outdoor activity of children increased by one hour per week, the risk of myopia was reduced by about 2%, and the children with myopia were found to spend about 3.7 hours less per week outdoors than children with an emmetropic or hypermetropic eye. Further, according to a study conducted on Danish children, children having about 80 minutes of outdoor activities per day had less myopia than children not spending time for outdoor activities, and it was verified that the children's eyes grew normally during the long summer daytime but the children's eyes grew quickly in the winter when the daytime is relatively short.

However, light of some wavelengths included in the sunlight may exert a disadvantageous influence on the human eye. For example, a UV in some wavelength ranges included in the sunlight may cause a cataract (a clouding of the lens in the eye which leads to a decrease in vision), a pterygium (a disease in which a blood vessel and a fibrous tissue grow in cornea), and a photokeratitis (a disease in which a corneal epithelial cell becomes inflamed by transient burn).

As such, the light source according to an exemplary embodiment may not emit light having the wavelength range that causes the cataract, the pterygium, and the photokeratitis as in the sunlight, and provide light only in the wavelength range corresponding to the visible light. In this manner, a problem that may occur when receiving the sunlight outdoors for prevention and treat treatment purposes of the myopia, such as adjusting the hours of outdoor activities consideration time and intensity of ultraviolet light, may not take place, and there is little harm even when exposed to the light for a long period of time.

In addition, white light emitted from a conventional light source may not have an evenly distributed spectral spectrum as compared to the sunlight, and a blue light is strongly irradiated in general. When the human eye s continuously exposed to the excessive blue light, the risk of developing eye diseases, such as macular degeneration and cataracts, may be increased. As such, the light source according to an exemplary embodiment irradiates light with a relatively intensity in an entire length range without excessively radiating light of a specific wavelength. In this manner, side effects caused by the light exposure may be suppressed.

Figure 4A:
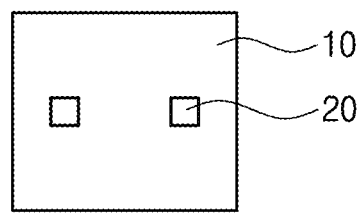
FIG. 4A is a schematic plan view of a light source according to an exemplary embodiment.

The above-described light source according to an exemplary embodiment may be implemented as a light emitting device package on which at least one chip is mounted. FIG. 4A is a schematic plan view of a light source according to an exemplary embodiment, and FIG. 4B is a cross-sectional view of the light source shown in FIG. 4A.

Figure 4B:
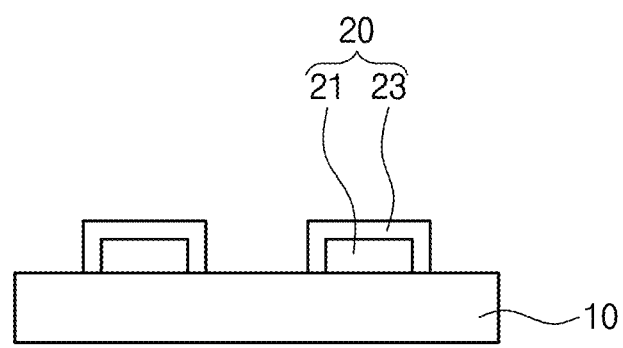
FIG. 4B is a cross-sectional view of the light source of FIG. 4A.

Referring to FIGS. 4A and 4B, the light source according to an exemplary embodiment includes a substrate 10 and at least one light emitting unit 20 disposed on the substrate 10. FIGS. 4A and 4B illustrate that the light source includes two light emitting units 20, i.e., a first light emitting unit and a second light emitting unit, however, the inventive concepts are not limited to a particular number of the light emitting units 20. For example, in some exemplary embodiments, a light source may include one or three or more light emitting units 20.

The light emitting unit 20 is an individual light emitting source, which is capable of individually implementing a specific spectral power distribution in the light source, to realize a white light.

The light emitting unit 20 includes a light emitting device 21 emitting light having a wavelength range corresponding to a purple color among ultraviolet lights or visible lights, and a light conversion layer 23 disposed on the light emitting device 21 to convert the light from the light emitting device 21. The light conversion layer 23 may include first, second, and third fluorescent substances that convert the ultraviolet light or light having the wavelength range corresponding to the purple color emitted from the light emitting device 21 into light having wavelength ranges respectively corresponding to blue, green, and red colors.

In the light emitting device 21 according to an exemplary embodiment, the wavelength range of light may be in a range from about 290 nm to about 390 nm corresponding to the wavelength range of the ultraviolet light, or in a range from about 290 nm to about 320 nm. In the light emitting device 21 according to an exemplary embodiment, the wavelength range of the light may be in a range from about 400 nm to about 470 nm corresponding to the wavelength range of the purple visible light.

The light conversion layer 23 is disposed on the light emitting device 21. The light conversion layer 23 may be coated on the light emitting device 21 or attached to the light emitting device 21 after being manufactured separately.

The light conversion layer 23 absorbs light emitted from the light emitting device 21, and emits light having a different wavelength range. The light conversion layer 23 may include a quantum dot and/or a fluorescent substance. In the illustrated exemplary embodiment, the fluorescent substance may be used as the light conversion layer 23.

When the fluorescent substance is used as the light conversion layer 23, at least one or more of various fluorescent substances, such as a YAG-based fluorescent substance, a LuAG fluorescent substance, a beta SiAlON fluorescent substance, an alpha SiAlON fluorescent substance, a CASN fluorescent substance, and a silicate BAM fluorescent substance, may be used as the fluorescent substance, may be used.

The YAG-based fluorescent substance may generally emit light of a yellow wavelength, and may emit light in a wavelength range from yellowish orange to green depending on the addition of Gd and Ga. In the YAG-based fluorescent substance, when Gd is added and an amount of Gd increases, the spectrum shifts to a longer wavelength, and when Ga is added and an amount of Ga increases, the spectrum shifts to a shorter wavelength.

The LuAG-based fluorescent substance may mainly emit light of a yellow-green wavelength, and may produce a cyan color when Ga is added.

The beta SiAlON fluorescent substance is suitable for emitting light in the green wavelength range, and the alpha SiAlON fluorescent substance is suitable for emitting light in an amber wavelength range. In addition, the CASN (CaSlSiN)-based fluorescent substance is suitable for emitting light in a red wavelength range.

According to an exemplary embodiment, the fluorescent substance may convert light emitted from the light emitting device 21 to light having wavelength ranges respectively corresponding to the blue, green, and red colors. When the fluorescent substances that convert light into light having wavelength ranges corresponding to the blue, green, and red colors are respectively referred to as the first, second, and third fluorescent substances, the first fluorescent substance may be at least one of $BaMgAl_{10}O_{17}:Mn^{2+}$, $BaMgAl_{12}O_{19}:Mn^{2+}$, or $Sr,Ca,Ba(PO_4)Cl:Eu^{2+}$, the second fluorescent substance may be at least one of $LuAG(Lu_3(Al,Gd)5_{12}:Ce^{3+})$, $YAG(Y_3(Al,Gd)_5O_{12}:Ce^{3+})$, $Ga-LuAG(Lu,Ga)_3(Al,Gd)_5O_{12}:Ce^{3+}$, $Ga-YAG(Ga,Y)_3(Al,Gd)_5O_{12}:Ce^{3+}$, $LuYAG(Lu,Y)_3(Al,Gd)_5O_{12}:Ce^{3+}$), Ortho Silicate, BOSE (($Sr,Ba,Ca,Mg)_2SiO_4:Eu^{2+}$), Oxynitride ($Ba,Sr,Ca)Si_2O_2N_2:Eu^{2+}$), or ThioGallate($SrGa_2S_4:Eu^{2+}$), and the third fluorescent substance may be at least one of $CASN(CaAlSiN_3:Eu^{2+})$, Oxynitride(($Ba,Sr,Ca)_2Si_5N_8:Eu^{2+}$), Sulfide($Ca,Sr)S_2:Eu^{2+}$), or Thio-Silicate(($Sr,Ca)_2SiS_4:Eu^{2+}$).

In an exemplary embodiment, the first light emitting unit and the second light emitting unit may include the same light emitting device 21 and the same first to third fluorescent substances. More particularly, the spectrum of light emitted from the first light emitting unit may be the same as the spectrum of light emitted from the second light emitting unit. However, the inventive concepts are not limited thereto, and in some exemplary embodiments, a combination of the light emitting device 21 of the first and second light emitting units and the first to third fluorescent substances may be variously changed.

For example, the light emitting device 21 of the first light emitting unit may emit an ultraviolet light of a predetermined wavelength range, and the light emitting device 21 of the second light emitting unit may emit an ultraviolet light of a wavelength range different from that of the first light emitting unit. The first to third fluorescent substances that convert light emitted from each light emitting device 21 of the first and second light emitting units may be combined in various concentrations and shapes, depending on a light profile of each light emitting device 21 of the first and second light emitting units. Accordingly, light finally emitted from the light source has a spectrum substantially similar to that of a solar light as a whole.

As described above, the number of the light emitting units 20 may be three or more, and may further include an additional unit to convert the color of the emitted light into cyan, yellow, and amber colors, as well as the blue, green, and red colors.

In this case, the spectrum of light is determined by light emitted from each of the first to third fluorescent substances, and light emitted from each of the first to third fluorescent substances has a broad spectrum as compared with light emitted from the light emitting device, and thus, light similar to the sunlight may be obtained. However, the inventive concepts are not limited to a particular fluorescent substance, and may be replaced with another fluorescent substance capable of obtaining an equivalent spectrum.

According to an exemplary embodiment, when the light emitting unit 20 is provided in plural, the light emitting units 20 may be driven together or separately. As such, the light source may emit a fixed light to have a predetermined color temperature, or may emit light that is variable to have different color temperatures depending on therapy conditions. For example, the light source according to an exemplary embodiment may be operated to emit cool white light for a predetermined time period and to emit warm white light for another predetermined time period.

The light source having the above-described structure according to the exemplary embodiments may be employed in various types of devices for eye therapy.

Figure 5:
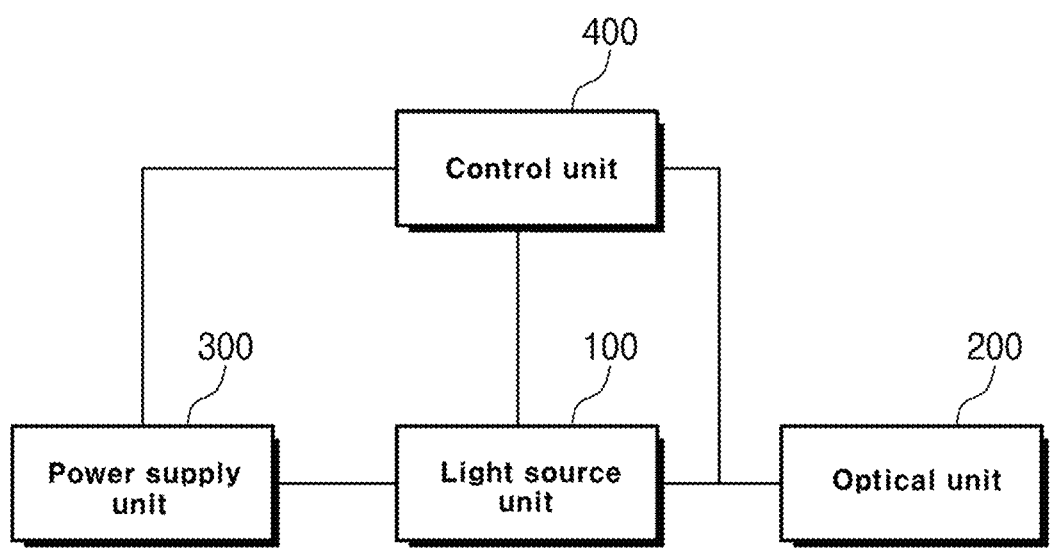
FIG. 5 is a block diagram of a light emitting device for an eye therapy according to an exemplary embodiment.

FIG. 5 is a block diagram of a device for the eye therapy according to an exemplary embodiment.

Referring to FIG. 5, the device for the eye therapy may include a light source unit 100 emitting light similar to the sunlight, a control unit 400 controlling the light source unit 100, a power supply unit 300 supplying a power to the light source unit 100, and the control unit 400.

The light source unit 100 includes a light source including a light emitting device and a fluorescent substance according to exemplary embodiments. The light emitting device may include a light emitting diode (LED), and a light source of a specific wavelength or that is capable of converting a wavelength. The light source capable of converting the wavelength may include a single light source or a plurality of light source to selectively emit light.

The control unit 400 may control an output of light, an amount of light, an intensity of light, and an emission time of light, which is emitted from the light source unit 100 in various ways, such as a continuous emission of light, emission of light while flickering, and a combination thereof.

The power supply unit 300 is electrically connected to the light source unit 100 and the control unit 400 to supply the power to the light source unit 100 and the control unit 400.

The device for the eye therapy may further include an optical unit 200 that focuses or scatters light emitted from the light source unit 100. The optical unit 200 may focus light generated from the light source unit 100 in a narrow range or a wide range depending on area of treatment. As another example, the optical unit 200 may focus or scatter light in a uniform or non-uniform manner depending on the location of treatment. In some exemplary embodiments, the optical unit 200 may include at least one lens that may perform various functions, e.g., focusing, scattering, uniformizing, and non-uniformizing functions, on the light from the light source unit 100. For example, when light is to be irradiated onto a small affected area from the light source, the lens used to focus light may be applied to the optical unit 200. As another example, when light is to be provided to a wide area, for example, an entire room from the light source, the lens used to scatter the light may be applied to the optical unit 200. In some exemplary embodiments, the optical unit 200 may be omitted.

Figure 6:
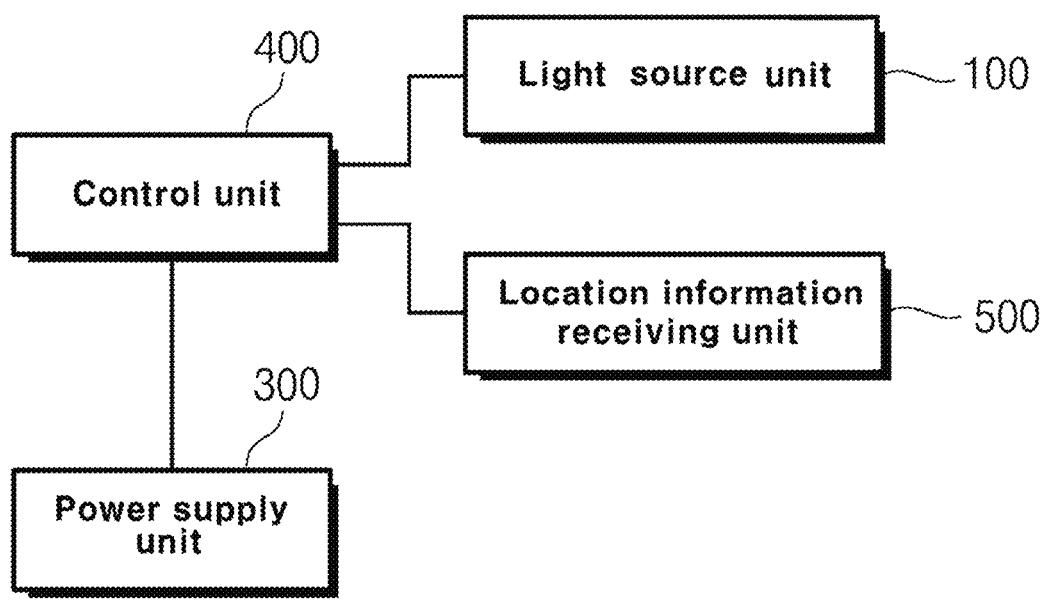
FIG. 6 is a block diagram of a light emitting device for an eye therapy according to another exemplary embodiment.

FIG. 6 is a block diagram of a light emitting device for an eye therapy according to another exemplary embodiment.

Referring to FIG. 6, the device for the eye therapy may include a light source unit 100 emitting a light similar to the sunlight, a location information receiving unit 500 receiving location information, and a control unit 400 receiving the location information from the location information receiving unit 500 and controlling a dose of light emitted from the light source unit 100. In an exemplary embodiment, the location information may include information obtained from a global positioning system (GPS).

As described above, the light source unit 100 may emit light having a wavelength range similar to that of the sunlight.

The location information receiving unit 500 may receive the location information from a satellite using the GPS, and may check current location information of the device for the eye therapy. The location information may include latitude and longitude information. The location information is provided to the control unit 400.

The control unit 400 may calculate the dose of light to be emitted from the light source unit 100 based on the location information provided from the location information receiving unit 500, and may control the light source unit 100 to emit light by the dose.

A power supply unit 300 is electrically connected to the light source unit 100, the location information receiving unit 500, and the control unit 400 to supply a power to the light source unit 100, the location information receiving unit 500, and the control unit 400. In FIG. 6, the light source unit 100 is shows as being connected to the location information receiving unit 500 via the control unit 400, however, the inventive concepts are not limited thereto. For example, in some exemplary embodiments, the light source unit 100 and the location information receiving unit 500 may be directly connected to the power supply unit 300.

The sunlight is not irradiated to the same extent in every places on earth. The sunlight is irradiated with a higher dose as the latitude decreases, and the sunlight is irradiated with a lower dose as the latitude increases. In addition, the sunlight is irradiated with a higher dose as an altitude becomes higher, and the sunlight is irradiated with a lower dose as the altitude becomes lower. Accordingly, a time of exposure to the sunlight or a degree of exposure to the sunlight may vary depending on the location of the user on earth.

In an exemplary embodiment, light corresponding to an average dose of the sunlight may be irradiated on the user after identifying a location of the device for the eye therapy, based on the location information and calculating the average dose of the sunlight at the identified location. Therefore, the human body may have the effect of being exposed to the sunlight by being irradiated with light from the device for the eye therapy according to an exemplary embodiment. In this case, the dose of light provided from the device for the eye therapy may be set within a range, which is harmless to the human body.

This will be described in more detail below with reference to the drawings.

Figure 7:
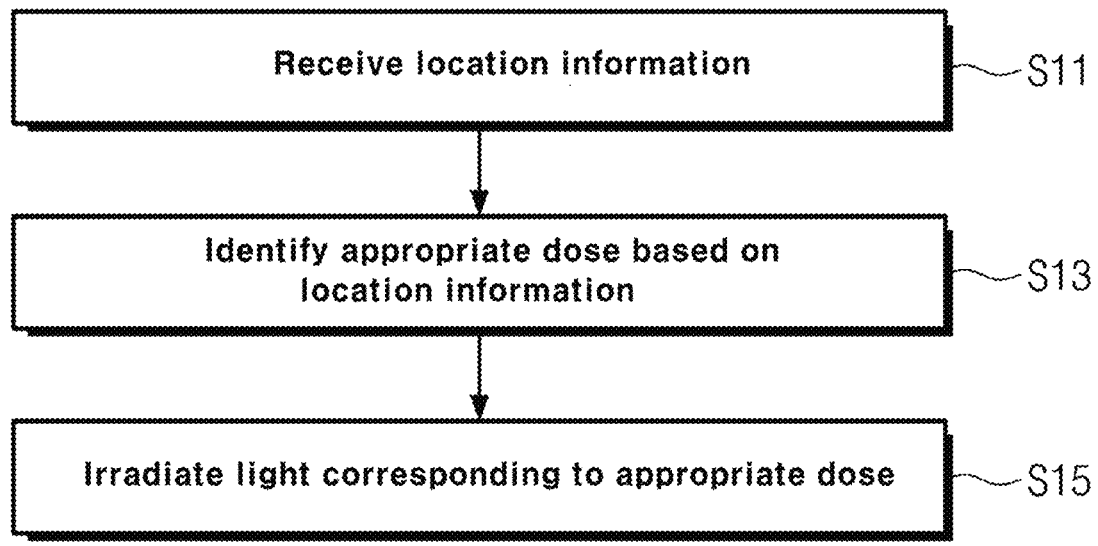
FIG. 7 is a flowchart showing an operation of a light emitting device for an eye therapy according to an exemplary embodiment.

FIG. 7 is a flowchart illustrating an operation of the device for the eye therapy of FIG. 6.

Referring to FIG. 7, the location information receiving unit receives the location information from the satellite (S11). The current location of the device for the eye therapy may be identified according to the location information. For example, it may be determined that the device for the eye therapy is located in B city of A country.

The location information is provided to the control unit. The control unit identifies an appropriate dose of light to be emitted by the device for the eye therapy based on the location information (S13). For example, when the current location of the device for the eye therapy is identified as B city of A country, information, such as sunrise time, sunset time, and average amount of sunshine, may be calculated by the control unit in addition to the latitude and longitude information in B city of A country. The control unit may determine whether it is daytime or nighttime by using an algorithm that calculates the sunrise and sunset times based on current latitude and longitude. As another example, the information, such as the sunrise time, the sunset time, and the average amount of sunshine, may be stored in a separate memory in the control unit, or may be obtained by accessing an internet network.

The control unit may calculate a turn-on time, a turn-off time, and an intensity of light of the light source unit based on the information, such as the sunrise time, the sunset time, and the average amount of sunshine, so that the dose of light becomes similar to that of actual sunlight, that is, the appropriate dose. In particular, the control unit may appropriately control whether to irradiate light from the light source unit by determining whether it is the daytime or nighttime without a separate illuminance sensor or the like.

The control unit turns on or off the light source unit to allow light corresponding to the calculated appropriate dose to be irradiated to the user from the light source unit (S15). In this manner, the user may be irradiated by light with substantially the same dose as the sunlight based on the user's location even though the user may be at indoors.

According to an exemplary embodiment, even when the user is in an environment where it is difficult to be exposed to the sunlight, such as living indoors for a long period time, staying in a patient room or in a limited space, or working mostly at night, the user may be provided with light similar to the sunlight in an appropriate dose for a suitable period of time at the user's current location. Accordingly, the user may stay in a familiar environment and become psychologically stable. In addition, the user may control the irradiation time of light by taking into account the sunrise or sunset time, which may refresh a circadian rhythm of the user.

In the above-described exemplary embodiments, the device for the eye therapy may be used in lieu of the sunlight based on the location information, however, the inventive concepts are not limited thereto. For example, in some exemplary embodiments, the device for the eye therapy according to an exemplary embodiment may be used as a complementary light source unit that compensates for a deficient light similar to the sunlight, while providing light similar to the sunlight, e.g., a deficient dose or a deficient wavelength range compared to the sunlight. In addition, when an external light generated by another light source other than the sunlight exists, the device for the eye therapy according to an exemplary embodiment may be used as a complementary light source unit that compensates for a deficiency of the external light, e.g., a deficient dose or a deficient wavelength range compared to the external light. Hereinafter, the device for the eye therapy used as the complementary light source unit that compensates for the deficiency of the sunlight will be described.

The amount of sunshine at a high-latitude location may be significantly lower than that at a low-latitude location. When the amount of sunshine is low, there may be a deficiency of light in an ultraviolet wavelength range as well as in a visible light wavelength range, which is irradiated to the user. The device for the eye therapy according to an exemplary embodiment may additionally irradiate light in the ultraviolet wavelength range and the light in the visible light wavelength range that are deficient, and thus, may compensate sunlight.

Figure 8:
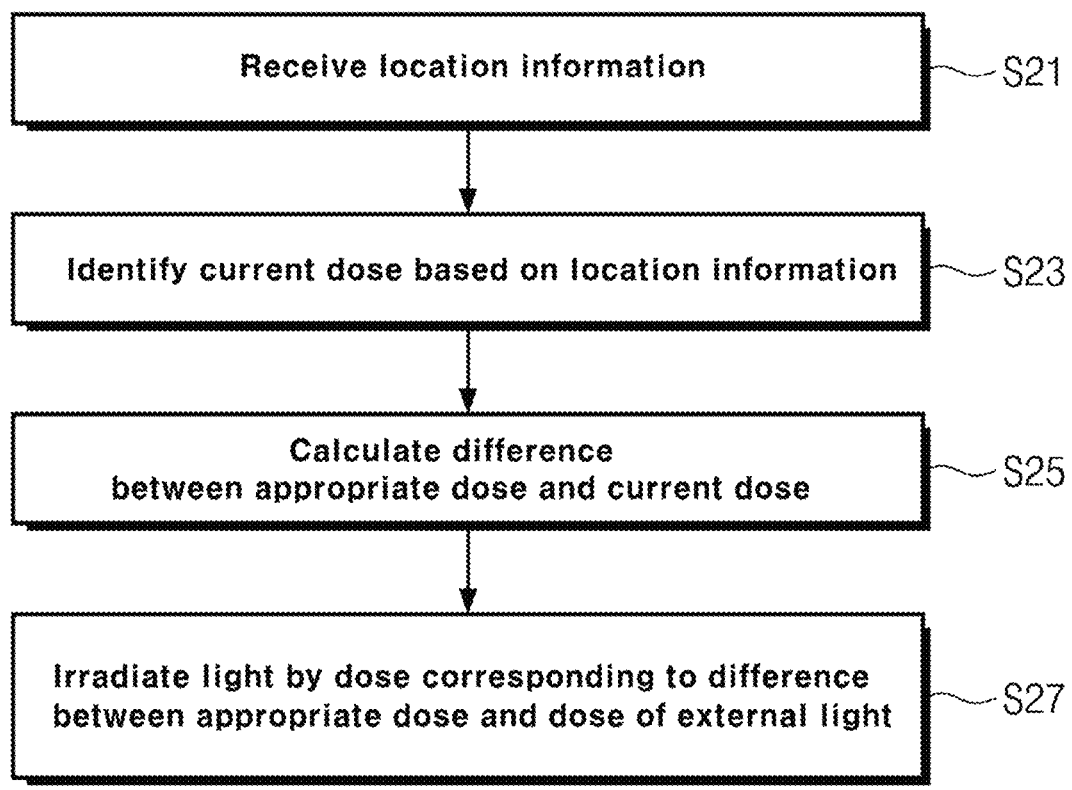
FIG. 8 is a flowchart showing an operation of a light emitting device for an eye therapy according to another exemplary embodiment.

FIG. 8 is a flowchart illustrating an operation of a light emitting device for an eye therapy according to another exemplary embodiment.

Referring to FIG. 8, the location information receiving unit receives the location information from the satellite (S21). The location information receiving unit may determine that the device for the eye therapy is located in D city of C country.

The location information is provided to the control unit. The control unit calculates the information, such as the sunrise time, the sunset time, and the average amount of sunshine, at a current location based on the location information, and calculates the dose of the sunlight at the current location based on the information, such as the sunrise time, the sunset time, and the average amount of sunshine (S23).

Then, a difference in dose between the appropriate dose of the light required for the user and the dose of the sunlight at the current location is calculated (S25). For example, when D city of C country is located at high latitude, the dose of the sunlight at the location of D city may be smaller than the dose of the sunlight required for the human body. When assuming that the dose of the sunlight required for the human body is the appropriate dose, a value obtained by subtracting the current dose of the sunlight from the appropriate dose is a dose that is insufficient. The appropriate dose of light required for the user may be already stored in a separate memory in the control unit, or may be easily obtained by accessing an internet network.

The control unit turns on or off the light source unit to allow light with the dose corresponding to the difference between the appropriate dose and the current dose of the sunlight, i.e., the insufficient dose, to be irradiated to the user from the light source unit (S27).

The user may be irradiated with a predetermined light at the dose that is most appropriate to the user, regardless of the user's location.

In an exemplary embodiment, the light source unit may be provided in plural, and in this case, the light source units may each emit light having different wavelength ranges from each other. The light source units may be substantially simultaneously driven or independently driven.

Figure 9A:
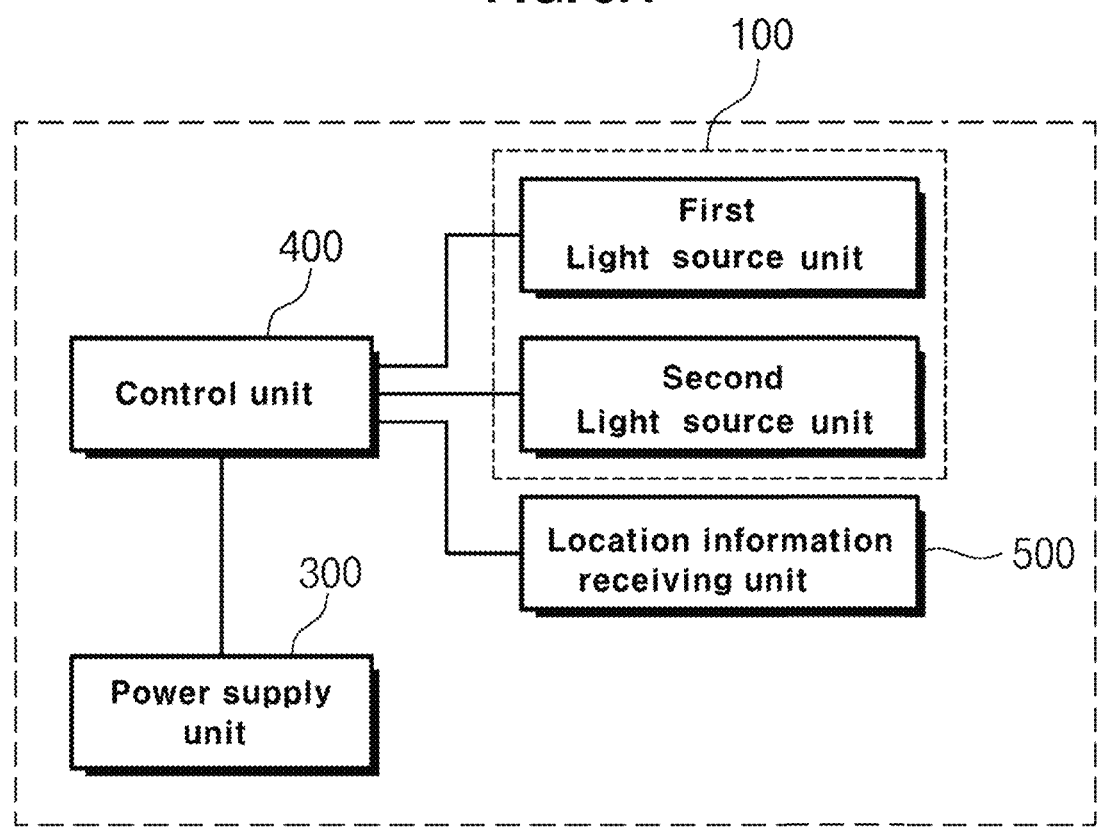
FIG. 9A is a block diagram of a light emitting device for an eye therapy according to an exemplary embodiment.
Figure 9B:
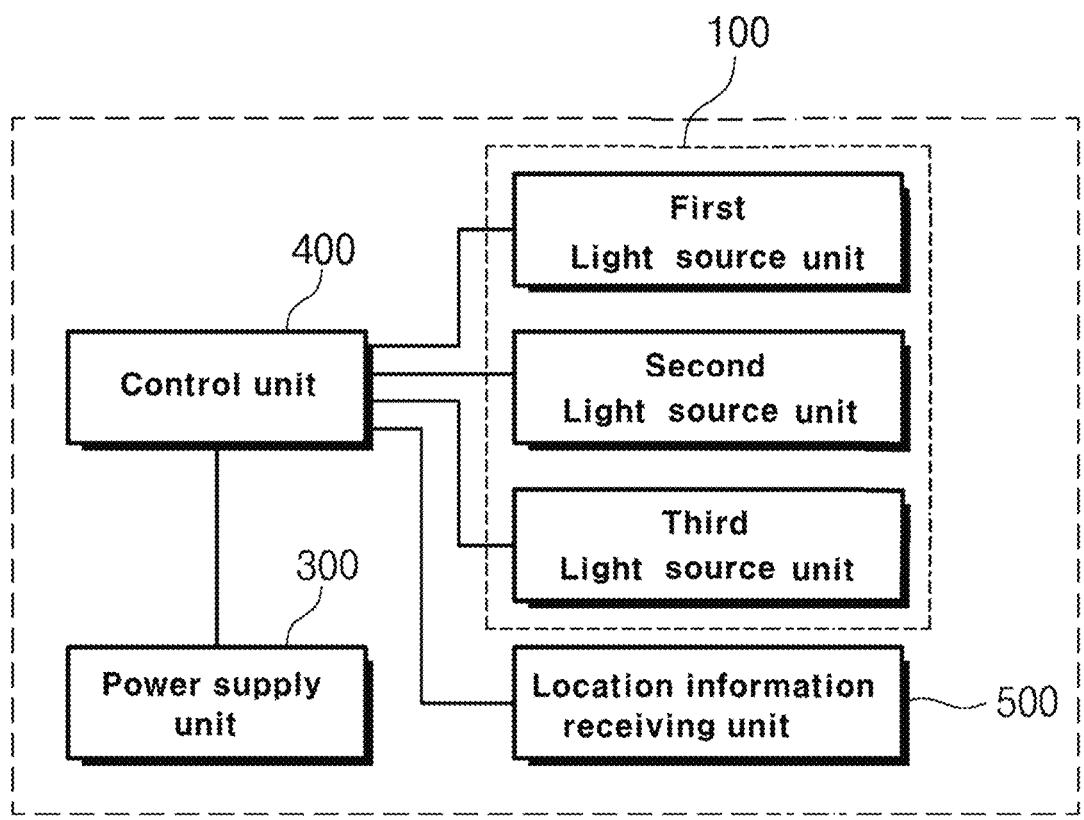
FIG. 9B is a block diagram of a light emitting device for an eye therapy according to another exemplary embodiment.

FIG. 9A is a block diagram of a light emitting device for an eye therapy, which includes two light sources, i.e., a first light source and a second light source, according to another exemplary embodiment. FIG. 9B is a block diagram of a light emitting device for an eye therapy, which includes three light sources, i.e., a first light source, a second light source, and a third light source, according to another exemplary embodiment. FIGS. 9A and 9B illustrated two or three light sources, however, the inventive concepts are not limited to a particular number of light sources in the light emitting device. For example, in some exemplary embodiments, the light source may be provided in different numbers.

Referring to FIG. 9A, the light source unit may include a first light source emitting a light in a first wavelength range and a second light source emitting a light in a second wavelength range different from the first wavelength range.

According to an exemplary embodiment, the first light source may emit light in a wavelength range similar to the sunlight as described above, and the second light source may emit light in the ultraviolet wavelength range. In another exemplary embodiment, the second light source may emit light in the infrared or near infrared wavelength range. Further, in some exemplary embodiments, the second light source may emit light in the blue wavelength range.

Referring to FIG. 9B, the light source unit may include a first light source emitting a light in a first wavelength range, a second light source emitting a light in a second wavelength range different from the first wavelength range, and a third light source emitting a light in a third wavelength range different from the first and second wavelength ranges. The first to third light sources may be independently driven, and thus, the first to third light sources may be combined with each other in various ways. In this case, the control unit may individually provide each light or may mix light emitted from at least two of the light sources.

In an exemplary embodiment, the first light source may emit light in a wavelength range similar to the sunlight as described above, the second light source may emit light in the visible wavelength range, and the third light source may emit light in the infrared wavelength range. In another exemplary embodiment, the first light source may emit light in the wavelength range similar to the sunlight as described above, the second light source may emit light in the ultraviolet wavelength range, and the third light source may emit light in the blue wavelength range. In some exemplary embodiments, the first light source may emit light in the wavelength range similar to the sunlight as described above, the second light source may emit light in a red or near infrared wavelength range, and the third light source may emit light in the ultraviolet wavelength range.

As described above, in an exemplary embodiment, additional effects may be obtained by compensating light that is deficient in a certain wavelength. For example, when light in the red or near infrared wavelength range is compensated, an immune mechanism may be activated during wound treatment. In addition, when light in the blue wavelength range or the light in the ultraviolet wavelength range is compensated, a sterilization effect on pathogen may be obtained.

Light in the red to near infrared wavelength range is applied to a skin to expand blood vessels and to promote blood circulation. More particularly, light in the red to near infrared wavelength range improves blood flow, and thus, stimulates the immune system of the human body. Light in the red to near infrared wavelength range may correspond to light in a wavelength range from about 610 nm to about 940 nm. In an exemplary embodiment, light in the red to near infrared wavelength range may be light in the red visible light wavelength range, e.g., from about 610 nm to about 750 nm, or may be light in the infrared wavelength range, e.g., from about 750 nm to about 940 nm. As another example, light in the red to near infrared wavelength range may be light having a wavelength of about 830 nm, about 850 nm, or of about 890 nm in the infrared wavelength range.

Light in the blue wavelength range may be effective in photosensitizers for pathogens, such as microorganisms, e.g., bacteria, virus, and fungi, to cause damage to cells of the microorganisms, to thereby induce a death of the microorganisms. In an exemplary embodiment, light in the blue wavelength range may be light in a wavelength range from about 400 nm to about 420 nm. In particular, light in the blue wavelength range according to an exemplary embodiment may be light in a wavelength of about 405 nm.

Light in the ultraviolet wavelength range has the effect of killing the pathogens, such as bacteria, virus, and fungi. When an ultraviolet light is applied to an infectious agent, DNA in the infectious agent absorbs the ultraviolet light, and the energy of the ultraviolet light changes a DNA structure. The changed DNA leads to the death of the infectious agent because of its inability to proliferate. The ultraviolet light may be light in a wavelength range from about 100 nm to about 400 nm, and may be a UVA, UVB, or UVC. The UVA may have a wavelength range from about 315 nm to about 400 nm, the UVB may have a wavelength range from about 280 nm to about 315 nm, and the UVC may have a wavelength range from about 100 nm to about 280 nm.

In an exemplary embodiment, when the ultraviolet light is irradiated, the light amount may be changed in various ways, however, a total dose to an object to be sterilized is set within a range that would be harmless to the human body. In addition, the light amount of the ultraviolet light is set to a dose range that is harmless to the human body with no light burn, to an extent that synthesis of vitamin D is promoted.

According to an exemplary embodiment, ultraviolet light may be irradiated at different values depending on the altitude of the sun, and the dose causing a sunburn may also be different. As such, the dose of the ultraviolet light of the sunlight may become different depending on the location on the earth, and the dose causing the sunburn may also be different. Accordingly, the dose required for a person at a predetermined location and a maximum allowable dose for the person at the predetermined location may be set differently for each location. As such, the control unit according to an exemplary embodiment may control the light source unit based on the dose required for the person and the maximum allowable dose for the person.

According to the above, the device for the eye therapy according to an exemplary embodiment may provide the human body with light that corresponds to the sunlight, or light whose dose is appropriately adjusted as needed.

In the device for the eye therapy according to an exemplary embodiment, the light amount and intensity of light emitted from the light source unit may be set in a variety of modes, and the user may select one mode among the various modes to receive light according to the selected mode.

For example, when the device for the eye therapy includes the first to third light sources, the light sources may be controlled in various ways, such as a first mode in which only the first light source is turned on, a second mode in which the first light source and the second light source are turned on, a third mode in which the first light source and the third light source are turned on, and a fourth mode in which the first light source flickers and the second light source is turned on.

These modes may be automatically set or may be manually set by the user. As described above, the setting values of the device for the eye therapy may be easily changed according to conditions desired by the user.

The device for the eye therapy according to an exemplary embodiment may be applied to a variety of fields, where lighting and light therapy are required. For example, the device for the eye therapy may be used in medical facilities, such as operating rooms and hospitals, for public or personal hygiene device for eye therapy, as well as lighting devices in general places.

In particular, the device for the eye therapy according to an exemplary embodiment may be used for public treatment purposes by being applied to public facilities, public-use spaces, and public-use products, or may be used for personal treatment purposes by being applied to personal facilities, personal-use spaces, and personal-use products. In addition, the device for the eye therapy may not only be used as an eye therapy device, but may be used in other therapeutic devices.

The device for the eye therapy has been described above in the form of block diagram, however, the device for the eye therapy according to exemplary embodiments may be implemented in various ways.

FIGS. 10A to 10D are perspective views showing devices for the eye therapy according to exemplary embodiments.

Figure 10A:
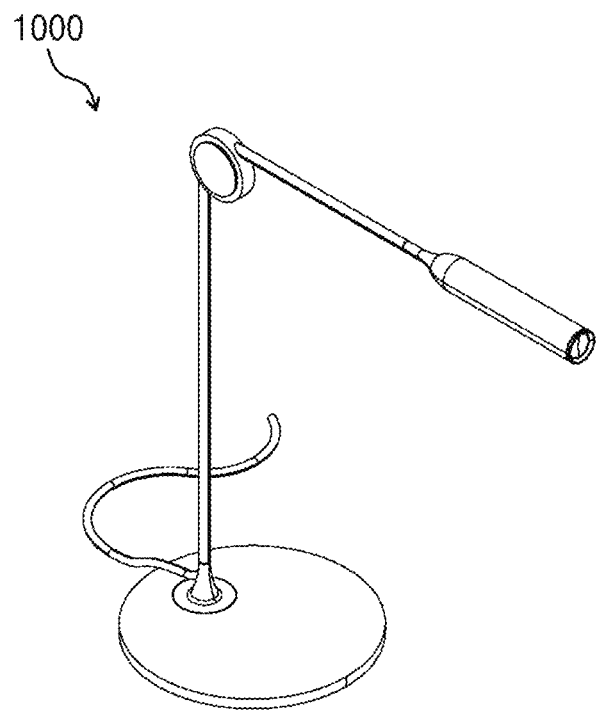
FIGS. 10A, 10B, 10C, and 10D are perspective views of devices for an eye therapy according to exemplary embodiments.

Referring to FIG. 10A, the device for the eye therapy according to an exemplary embodiment may be a lighting device, in particular, an indoor light device 1000.

Figure 10B:
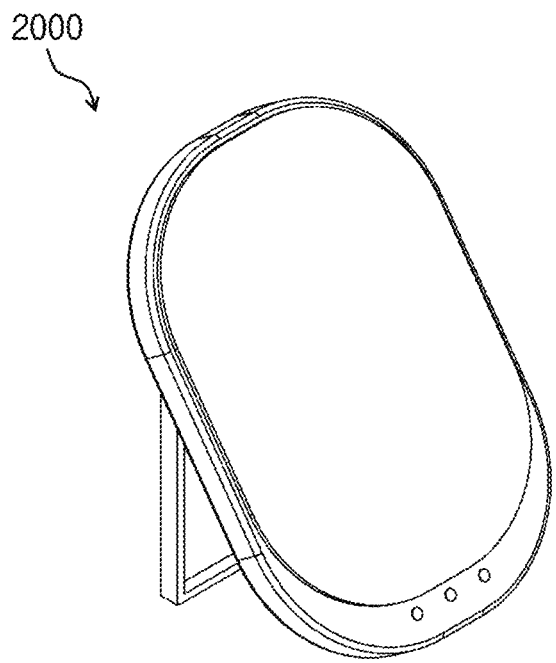

Referring to FIG. 10B, the device for the eye therapy according to an exemplary embodiment may be a personal lighting device 2000. The personal light device may be a table lamp, for example.

Figure 10C:
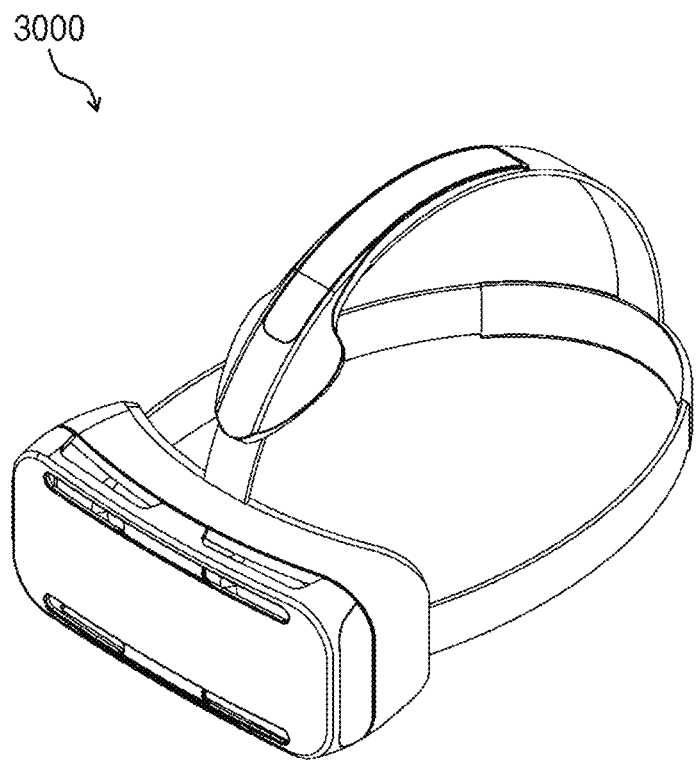

Referring to FIG. 10C, the device for the eye therapy according to an exemplary embodiment may be a head-mount display type therapy device 3000 that directly irradiates light onto the affected area.

Figure 10D:
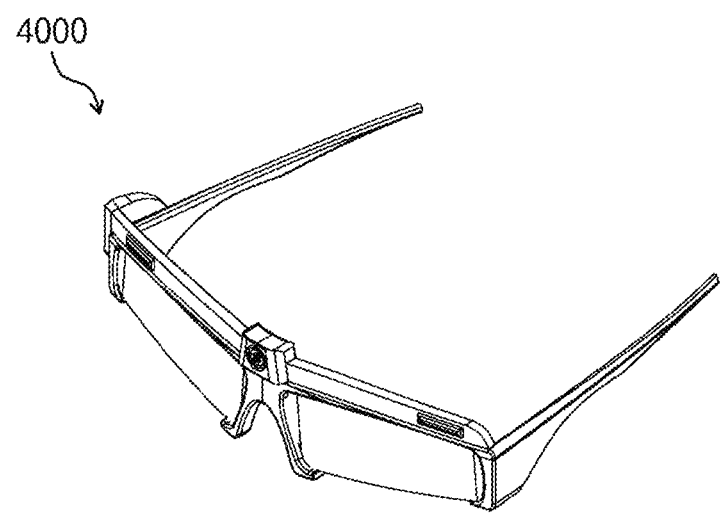
Figure 11A:
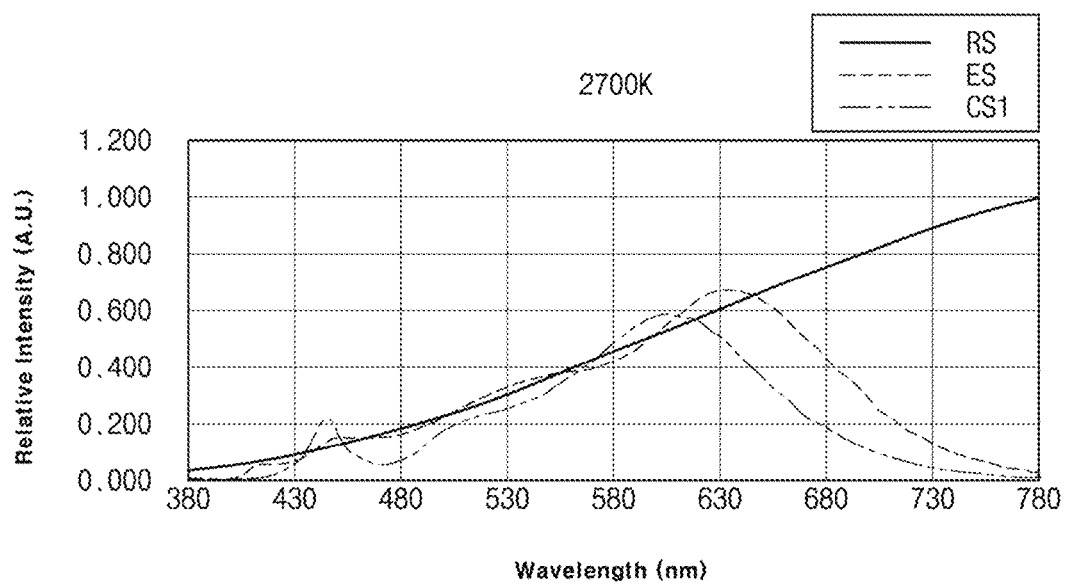
FIGS. 11A, 11B, 11C, 11D, and 11E are graphs showing spectra of a sunlight, a conventional LED light source, and a light source according to an exemplary embodiment as a function of a color temperature.
Figure 11B:
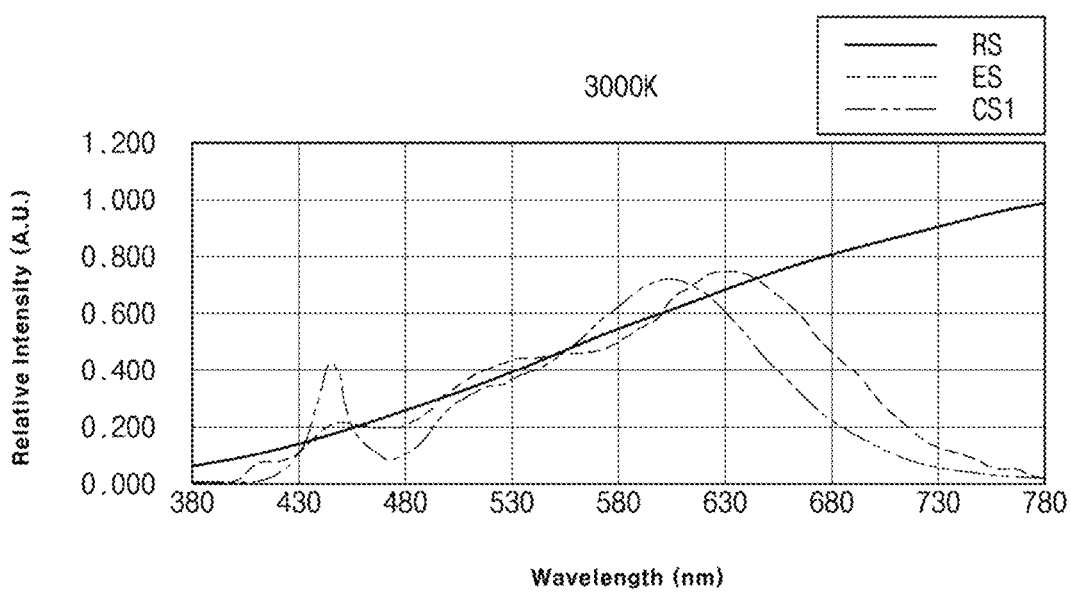
Figure 11C:
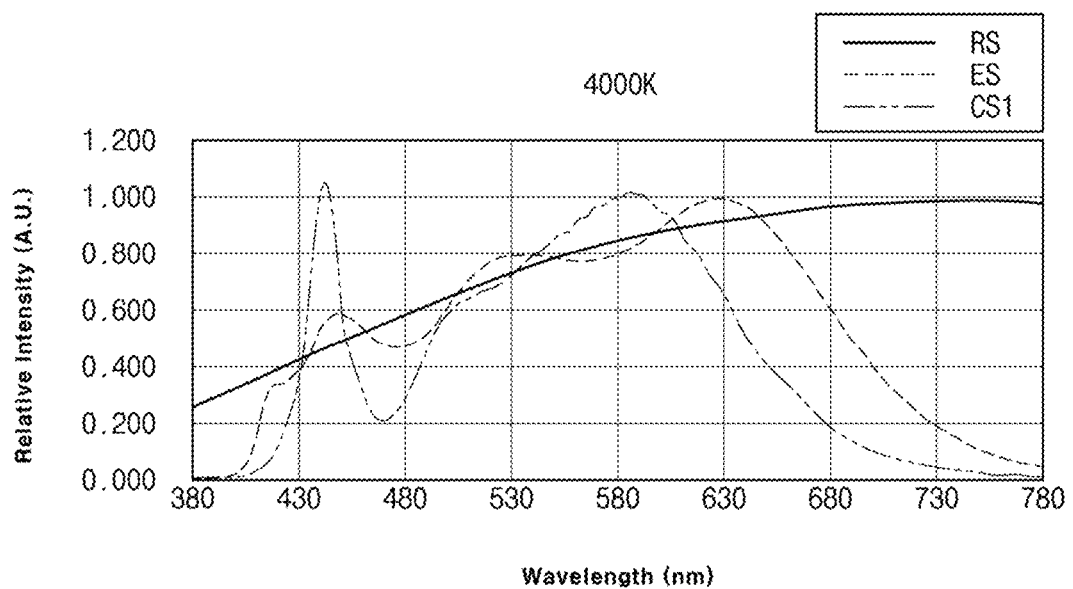
Figure 11D:
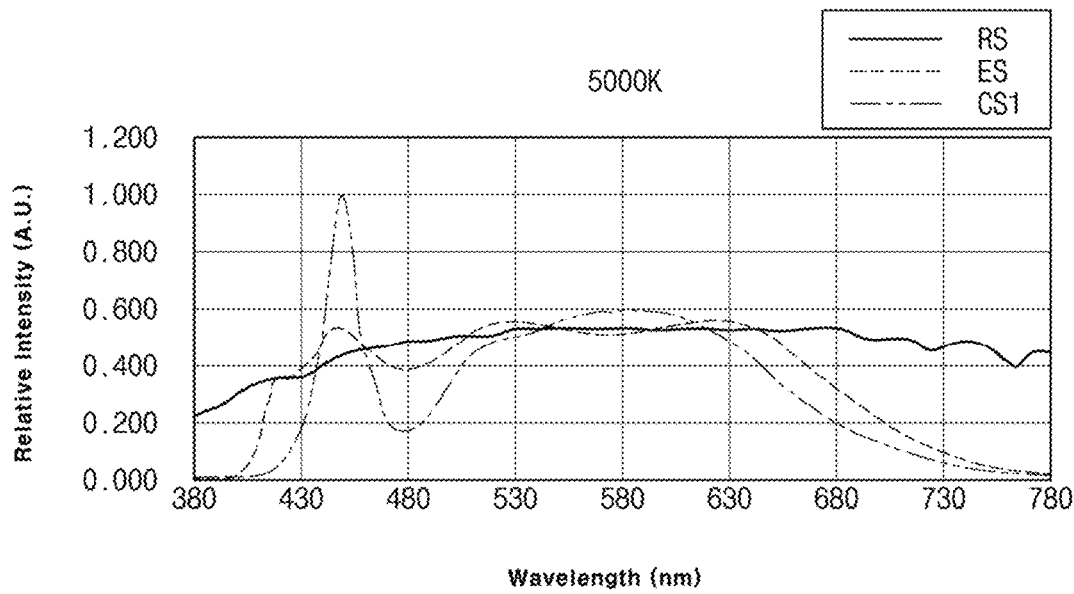
Figure 11E:
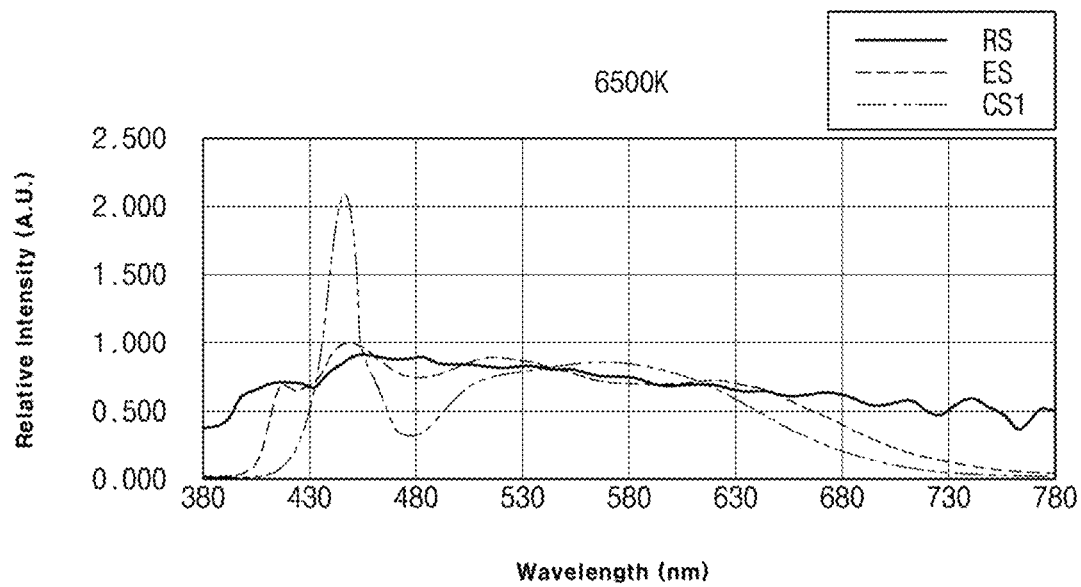

Referring to FIG. 10D, the device for the eye therapy according to an exemplary embodiment may be a glasses-type therapy device 4000 that directly irradiates the light onto the affected area.

As described above, the light source for the eye therapy according to an exemplary embodiment may be applied to various devices to allow a user to experience light very similar to the sunlight regardless of location and time. More particularly, since the light source for the eye therapy may be applied to various portable devices, there are few restrictions on places and times. Accordingly, the light source for the eye therapy according to the exemplary embodiments may provide various effects that may be obtained from the sunlight to people who are not exposed to the sunlight, such as ones working indoors for a long period time or working mainly at night.

FIGS. 11A to 11E are graphs showing spectra of the sunlight, the conventional LED, and the light source according to an exemplary embodiment as a function of the color temperature. In FIGS. 11A to 11E, a spectrum indicated by "RS" represents a solar spectrum, a spectrum indicated by "ES" represents a spectrum of the light emitted from the light source according to an exemplary embodiment, and a spectrum indicated by "CS1" represents a spectrum of a light emitted from the conventional LED. In particular, the conventional LED includes an LED emitting a blue light, and red and green fluorescent substances applied thereto.

Referring to FIGS. 11A to 11E, it may be seen that the light source according to an exemplary embodiment has the spectrum that is closer to the sunlight than the conventional LED in the entire visible light spectrum band.

The conventional LED shows the spectrum deviated from the solar spectrum in all measured color temperatures, as compared with the light source according to an exemplary embodiment. In particular, the conventional LED has a higher peak and a deeper valley than the sunlight and the light source according to an exemplary embodiment in the blue wavelength range among the visible light range. The conventional LED has the peak wavelength very higher than the sunlight and the light source according to an exemplary embodiment in the wavelength range from about 400 nm to about 450 nm. In addition, the conventional LED has the valley very lower than the sunlight and the light source according to an exemplary embodiment in the wavelength range from about 450 nm to about 490 nm. The light source according to an exemplary embodiment has the peak and the valley wavelengths in the wavelength range from about 400 nm to about 450 nm, and from about 450 nm to about 490 nm, however, the peak and the valley wavelengths of the light source according to an exemplary embodiment are respectively very lower and shallower than those of the conventional LED.

Table 2 below shows an area overlapping ratio between the spectra of the conventional LED and a solar light in the wavelength range from about 380 nm to about 780 nm, and an area overlapping ratio between the spectra of the light source according to an exemplary embodiment and the solar light in the wavelength range from about 380 nm to about 780 nm as a percentage. Referring to Table 2, the area overlapping ratio of the conventional LED is less than about 50% at a relatively low color temperature of about 2700K, while the area overlapping ratio of the light source according to an exemplary embodiment is about 59% at the color temperature of about 2700K. The area overlapping ratio of the light source according to an exemplary embodiment increases as the color temperature increases, which reaches to about 79% at the color temperature of about 6500K.

TABLE 2

| Color temperature | Conventional LED | Light source of embodiment of present disclosure |
|---|---|---|
| 2700 K | 44% | 59% |
| 3000 K | 51% | 62% |
| 4000 K | 58% | 70% |
| 5000 K | 63% | 75% |
| 6500 K | 66% | 79% |

Table 3 below shows the peak deviation of the conventional LED with respect to the solar spectrum in the wavelength range from about 380 nm to about 780 nm, and the peak deviation of the light source according to an exemplary embodiment with respect to the solar spectrum in the wavelength range from about 380 nm to about 780 nm. Referring to Table 3, the conventional LED has the peak deviation of about 0.11 at a relatively low color temperature of about 2700K, while the light source according to an exemplary embodiment has the peak deviation of about 0.07 at the color temperature of about 2700K. In addition, a difference between the peak deviation of the conventional LED and the peak deviation of the light source according to an exemplary embodiment with respect to the solar light spectrum increases as the color temperature increases. For example, the conventional LED has the peak deviation of about 1.23, however, the light source according to an exemplary embodiment has the peak deviation of about 0.14 at the color temperature of about 6500K.

TABLE 3

| Color temperature | Conventional LED | Light source of embodiment of present disclosure |
|---|---|---|
| 2700 K | 0.11 | 0.07 |
| 3000 K | 0.26 | 0.07 |
| 4000 K | 0.57 | 0.11 |
| 5000 K | 0.56 | 0.10 |
| 6500 K | 1.23 | 0.14 |

Table 4 below shows the peak deviation of the conventional LED and the peak deviation of the light source according to an exemplary embodiment with respect to the solar spectrum in the wavelength range from about 380 nm to about 490 nm, and the valley deviation of the conventional LED and the valley deviation of the light source according to an exemplary embodiment with respect to the solar spectrum in the wavelength range from about 450 nm to about 530 nm.

The peak and valley deviations shown in Table 4 are obtained using the method illustrated with reference to FIG. 3.

Referring to Table 4, the conventional LED has the peak deviation of about 0.11 with respect to the sunlight at the color temperature of about 2700K, while the peak deviation of the conventional LED increases as the color temperature increases. More particularly, the peak deviation is about 1.23 when the color temperature is about 6500K. This means that the difference in spectrum from the sunlight is large.

However, even though the peak deviation of the light source according to an exemplary embodiment increases as the color temperature increases, the peak deviation is equal to or less than about 0.14 as a whole, and thus, it may be confirmed that the difference in spectrum between the light source according an the exemplary embodiment and the sunlight is not large.

In addition, the conventional LED has the valley deviation of about 0.12 with respect to the sunlight at the color temperature of about 2700K, and the valley deviation of the conventional LED increases as the color temperature increases. More particularly, the valley deviation is about 0.57 when the color temperature is about 6500K. This means that the difference in spectrum from the sunlight is large.

However, even though the valley deviation of the light source according to an exemplary embodiment increases as the color temperature increases, the valley deviation is equal to or less than about 0.15 as a whole, and thus, it may be confirmed that the difference in spectrum between the light source according to an exemplary embodiment and the sunlight is not large.

TABLE 4

| | Peak deviation (380~490 nm) | | valley deviation (450~530 nm) | |
|---|---|---|---|---|
| Color temperature | Conventional LED | Light source of present disclosure | Conventional LED | Light source of present disclosure |
| 2700 K | 0.11 | 0.02 | 0.12 | 0.02 |
| 3000 K | 0.26 | 0.03 | 0.16 | 0.06 |
| 4000 K | 0.57 | 0.11 | 0.37 | 0.12 |
| 5000 K | 0.56 | 0.10 | 0.31 | 0.10 |
| 6500 K | 1.23 | 0.14 | 0.57 | 0.15 |

Figure 12A:
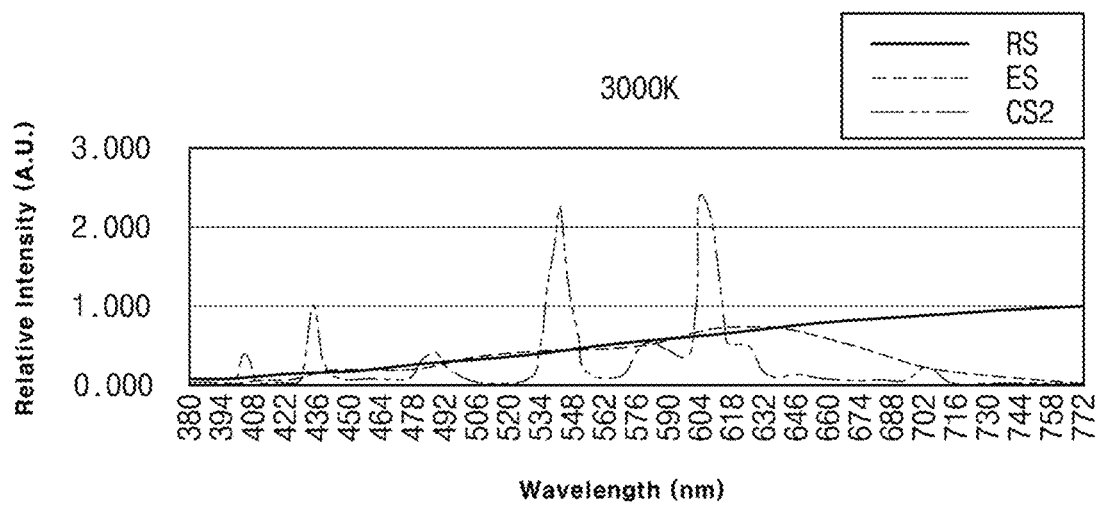
FIGS. 12A, 12B, and 12C are graphs showing spectra of a sunlight, a conventional fluorescent lamp, and a light source according to an exemplary embodiment as a function of a color temperature.
Figure 12B:
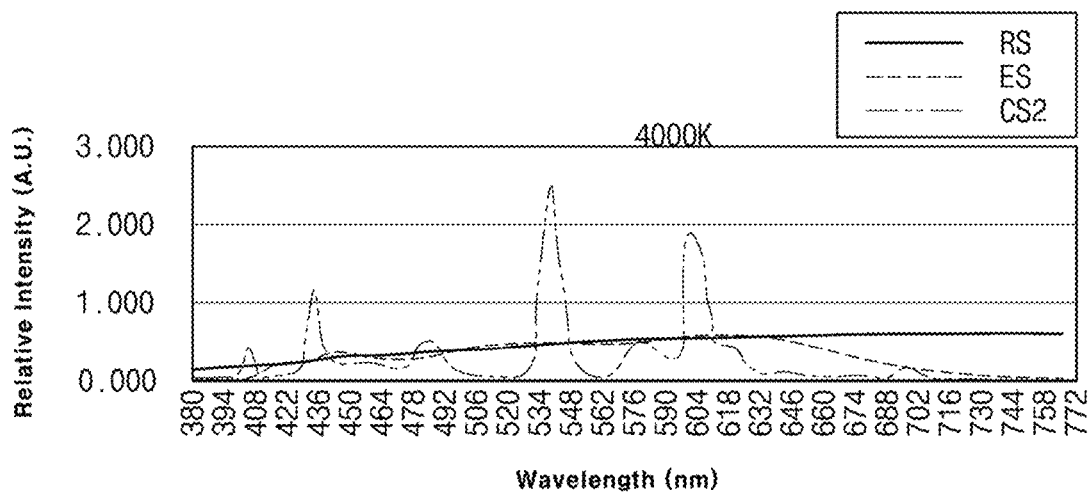
Figure 12C:
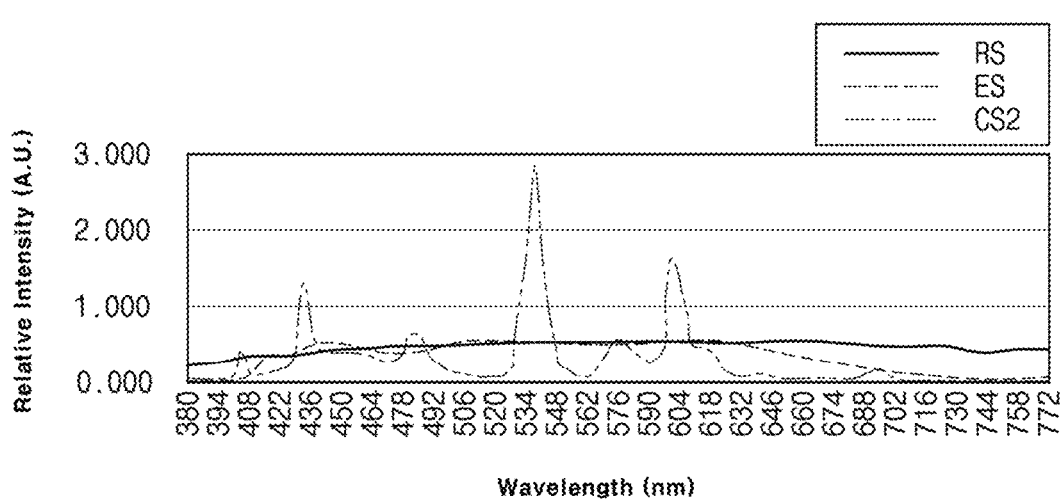

FIGS. 12A to 12C are graphs showing spectra of the sunlight, the conventional fluorescent lamp, and the light source according to an exemplary embodiment as a function of a color temperature.

In FIGS. 12A to 12C, a spectrum indicated by "RS" represents the solar spectrum, a spectrum indicated by "ES" represents the spectrum of light emitted from the light source according to an exemplary embodiment, and a spectrum indicated by "CS2" represents the spectrum of the light emitted from the conventional light source. As the conventional light source, the fluorescent lamp is used.

Referring to FIGS. 12A to 12C, it may be confirmed that the light source according to an exemplary embodiment has the spectrum closer to the sunlight than the conventional light source in the entire visible light spectrum band.

The conventional fluorescent lamp shows the spectrum extremely deviated from the solar spectrum in all measured color temperatures as compared with the light source according to an exemplary embodiment. In particular, the conventional fluorescent lamp has a higher peak and a deeper valley in the entire visible light range.

Table 5 below shows an area overlapping ratio between the spectra of the conventional fluorescent lamp and the solar light, and an area overlapping ratio between the spectra of the light source according to an exemplary embodiment and the solar light as a percentage. Referring to Table 5, the area overlapping ratio of the conventional fluorescent lamp is less than about 50% at a relatively low color temperature of about 3000K, while the area overlapping ratio of the light source according to an exemplary embodiment is about 62% at the color temperature of about 3000K. The area overlapping ratio of the light source according to an exemplary embodiment increases as the color temperature increases, which reaches to about 75% at the color temperature of about 6500K.

TABLE 5

| Color temperature | Conventional fluorescent lamp | Light source of present disclosure |
|---|---|---|
| 3000 K | 46% | 62% |
| 4000 K | 56% | 70% |
| 5000 K | 62% | 75% |

Table 6 below shows the peak deviation in spectrum between the conventional fluorescent lamp and the solar light in the wavelength range from about 380 nm to about 780 nm, and the peak deviation in spectrum between the light source according to an exemplary embodiment and the solar light in the wavelength range from about 380 nm to about 780 nm. Referring to Table 6, the conventional fluorescent lamp has a very large peak deviation of about 1.88 at a relatively low color temperature of about 3000K, and the peak deviation of the conventional fluorescent lamp increases as the color temperature increases. As such, the conventional fluorescent lamp has the peak deviation of about 2.30 at the color temperature of about 5000K. However, the light source according an exemplary embodiment has the peak deviation of about 0.07 to about 0.11 at the color temperature of about 3000K to about 5000K. As such, it may be seen that a spectrum similarity of the light source according to an exemplary embodiment with the sunlight is significantly higher than that of the fluorescent lamp.

TABLE 6

| Color temperature | Conventional fluorescent lamp | Light source of present disclosure |
|---|---|---|
| 3000 K | 1.88 | 0.07 |
| 4000 K | 3.46 | 0.11 |
| 5000 K | 2.30 | 0.10 |

Table 7 below shows the peak deviation of the conventional fluorescent lamp and the peak deviation of the light source according to an exemplary embodiment with respect to the solar spectrum in the wavelength range from about 380 nm to about 490 nm, and the valley deviation of the conventional fluorescent lamp and the valley deviation of the light source according to an exemplary embodiment with respect to the solar spectrum in the wavelength range from about 450 nm to about 530 nm.

The peak and valley deviations shown in Table 7 are obtained using the method illustrated with reference to FIG. 3.

Referring to Table 7, the conventional fluorescent lamp has the very large peak deviation equal to or greater than about 0.88 in the color temperature of about 3000K to about 5000K regardless of the color temperature. More particularly, the peak deviation is about 1.53 when the color temperature is about 4000K. This means that the difference in spectrum from the sunlight is large. However, the peak deviation of the light source according to an exemplary embodiment is changed slightly depending on the color temperature, however, the peak deviation is equal to or less than about 0.11 as a whole. As such, it may be seen that the difference in spectrum between the light source according to an exemplary embodiment and the sunlight is not large.

In addition, the conventional fluorescent lamp has the valley deviation equal to or greater than about 0.37 in the color temperature of about 3000K to about 5000K regardless of the color temperature. However, the valley deviation of the light source according to an exemplary embodiment is changed slightly depending on the color temperature, however, the valley deviation is equal to or less than about 0.12 as a whole. As such, it may be seen that the difference in spectrum between the light source according to an exemplary embodiment and the sunlight is not large.

TABLE 7

| Color temperature | Peak deviation (380~490 nm) | | valley deviation (450~530 nm) | |
|---|---|---|---|---|
| | Conventional fluorescent lamp | Light source of present disclosure | Conventional fluorescent lamp | Light source of present disclosure |
| 3000 K | 0.88 | 0.03 | 0.37 | 0.06 |
| 4000 K | 1.53 | 0.11 | 0.68 | 0.12 |
| 5000 K | 0.94 | 0.10 | 0.47 | 0.10 |

Table 8 below shows the peak deviation of the conventional fluorescent lamp and the peak deviation of the light source according to an exemplary embodiment with respect to the solar spectrum, and the valley deviation of the conventional fluorescent lamp and the valley deviation of the light source according to an exemplary embodiment with respect to the solar spectrum. In detail, Table 8 shows the peak deviation and the valley deviation in a predetermined range including the wavelength range of about 555 nm and about 490 nm.

Referring to Table 8, the conventional fluorescent lamp has the peak deviation equal to or greater than about 1.88 regardless of the color temperature, and this means that the difference in spectrum between the conventional fluorescent lamp and the sunlight is large. However, the light source according to an exemplary embodiment has the peak deviation from about 0.03 to about 0.05 depending on the color temperature, and thus, it may be seen that the difference in spectrum between the light source according to an exemplary embodiment and the sunlight is not large.

The conventional fluorescent lamp has the valley deviation equal to or greater than about 0.18 regardless of the color temperature, and this means that the difference in spectrum between the conventional fluorescent lamp and the sunlight is large. However, even though the valley deviation is changed slightly depending on the color temperature, the light source according to an exemplary embodiment has the valley deviation equal to or less than about 0.12, and thus, it may be seen that the difference in spectrum between the light source according to the exemplary embodiment of the present disclosure and the sunlight is not large.

TABLE 8

| Color temperature | Peak deviation (535~565 nm) | | valley deviation (460~490 nm) | |
|---|---|---|---|---|
| | Conventional fluorescent lamp | Light source of present disclosure | Conventional fluorescent lamp | Light source of present disclosure |
| 3000 K | 1.88 | 0.03 | 0.18 | 0.06 |
| 4000 K | 3.46 | 0.05 | 0.30 | 0.12 |
| 5000 K | 2.30 | 0.03 | 0.20 | 0.10 |

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light source for eye therapy configured to emit light having a wavelength range from 380 nm to 780 nm, and has a spectrum area that overlaps at least 55% of an area of a normalized solar spectrum,
wherein:
  a peak wavelength of the light has a deviation equal to or less than 0.14 from the normalized solar spectrum in a wavelength range from 380 nm to 490 nm;
  a color temperature of the light is in a range of 2600K to 7000K; and
  the deviation of the peak wavelength of the light increases as the color temperature of the light increases from 2600K to 4000K.

2. The light source of claim 1, wherein a valley wavelength of the light has a deviation equal to or less than 0.15 from the normalized solar spectrum in the wavelength range from 460 nm to 490 nm.

3. The light source of claim 2, wherein the spectrum area of the light overlaps at least 55% of the area of the normalized solar spectrum when the color temperature of the light is in a range of 2600K to 3700K.

4. The light source of claim 3, wherein a peak wavelength of the light has a deviation equal to or less than 0.10 from the normalized solar spectrum.

5. The light source of claim 2, wherein the spectrum area of the light overlaps at least 70% of the area of the normalized solar spectrum when the color temperature of the light is in a range from 3700K to 4700K.

6. The light source of claim 5, wherein the peak wavelength of the light has the deviation equal to or less than 0.13 from the normalized solar spectrum.

7. The light source of claim 2, wherein the spectrum area of the light overlaps at least 75% of the area of the normalized solar spectrum when the color temperature of the light is in a range from 4700K to 7000K.

8. The light source of claim 7, wherein the peak wavelength of the light has the deviation equal to or less than 0.14 from the normalized solar spectrum.

9. A light source for eye therapy, configured to emit light having a color temperature in a range of 2600K to 7000K,
wherein:
  a spectrum area of the light overlaps at least 55% of an area of a normalized solar spectrum;
  a peak wavelength of the light has a first deviation from the normalized solar spectrum in a wavelength range from 380 nm to 490 nm;
  a valley wavelength of the light has a second deviation from the normalized solar spectrum in the wavelength range from 380 nm to 490 nm that is equal to or greater than the first deviation; and
  a difference between the first deviation and the second deviation decreases as the color temperature of the light increases from 3000K to 5000K.

10. The light source of claim 9, wherein the peak wavelength of the light has the first deviation equal to or less than 0.14 from the normalized solar spectrum.

11. The light source of claim 9, wherein the normalized solar spectrum is represented by $$E(\lambda, T) = \frac{2hc^2}{\lambda^5} \cdot \frac{1}{e^{hc/\lambda kT} - 1},$$

where $\lambda$, $h$, $c$, $T$, and $k$ denote a wavelength (um), Planck's constant, a speed of light, an absolute temperature, and Boltzmann's constant, respectively.

12. The light source of claim 11, wherein the light source is used for treating myopia.

13. The light source of claim 11, wherein the light source is used for reducing eye stress.

14. A light emitting device for eye therapy, comprising:
  the light source of claim 9; and
  a control unit for controlling the light source.

15. The light emitting device of claim 14, further comprising a mounting member connected to the light source to be mounted on a user's head.

16. The light emitting device of claim 14, further comprising a supporting member for supporting the light source to be provided as a table lamp.

17. A light emitting diode for eye therapy, comprising:
  a first light source configured to emit light having a first wavelength range from 380 nm to 780 nm, wherein a spectrum area of the light overlaps at least 55% of an area of a normalized solar spectrum;
  a second light source configured to emit light in a ultra-violet wavelength range;
  a location information receiving unit configured to detect a location of the light emitting diode; and
  a control unit configured to adjust an amount of the light emitted from the first and second light sources in response to information obtained from the location information receiving unit,
wherein:
  a peak wavelength of the light emitted from the first light source has a deviation equal to or less than 0.14 from the normalized solar spectrum in a wavelength range from 380 nm to 490 nm;
  a color temperature of the light emitted from the first light source is in a range of 2600K to 6500K; and
  the deviation of the peak wavelength has the greatest value when the light emitted from the first light source has the color temperature of 6500K.

18. The light emitting diode of claim 17, further comprising a third light source configured to emit light in an infrared wavelength range,
  wherein the location information receiving unit comprises a global positioning system.

19. The light emitting diode of claim 18, wherein a peak wavelength of the light emitted from the first light source has a deviation equal to or less than 0.14 from the normalized solar spectrum in a wavelength range from 380 nm to 490 nm, and a valley wavelength of the light emitted from the first light source has a deviation equal to or less than 0.15 from the normalized solar spectrum in the wavelength range from 450 nm to 530 nm.

* * * * *